(12) United States Patent
Eckhof et al.

(10) Patent No.: US 12,114,895 B2
(45) Date of Patent: Oct. 15, 2024

(54) MODULAR SPINE STABILIZATION SYSTEM AND ASSOCIATED INSTRUMENTS

(71) Applicant: Xtant Medical Holdings, Inc., Belgrade, MT (US)

(72) Inventors: Stephan Eckhof, Rietheim-Weilheim (DE); Markus Salvermoser, Tuttlingen-Möhringen (DE); Rudolph Bertagnoli, Vienna (AT); William R. Sears, Warrawee (AU)

(73) Assignee: XTANT MEDICAL HOLDINGS, INC., Belgrade, MT (US)

( * ) Notice: Subject to any disclaimer, the term of this patent is extended or adjusted under 35 U.S.C. 154(b) by 0 days.

(21) Appl. No.: 18/111,687

(22) Filed: Feb. 20, 2023

(65) Prior Publication Data

US 2023/0200857 A1 Jun. 29, 2023

Related U.S. Application Data

(63) Continuation of application No. 16/723,072, filed on Dec. 20, 2019, now Pat. No. 11,583,318.

(Continued)

(51) Int. Cl.
*A61B 17/70* (2006.01)
(52) U.S. Cl.
CPC ...... *A61B 17/7026* (2013.01); *A61B 17/7014* (2013.01); *A61B 17/7083* (2013.01)
(58) Field of Classification Search
CPC ............ A61B 17/7026; A61B 17/7019; A61B 17/7028; A61B 17/863; A61B 17/7032–17/7035
See application file for complete search history.

(56) References Cited

U.S. PATENT DOCUMENTS 5,375,823 A 12/1994 Navas
5,658,286 A 8/1997 Sava
(Continued)

FOREIGN PATENT DOCUMENTS

CN 102106750 A 6/2011
DE 102014208012 B3 8/2015
(Continued)

OTHER PUBLICATIONS

International Search Report and Written Opinion for PCT/US2019/068059 mailed Apr. 27, 2020.
(Continued)

*Primary Examiner* — Julianna N Harvey
(74) *Attorney, Agent, or Firm* — Sheridan Ross P.C.

(57) ABSTRACT

An implantable, modular spine stabilization system that allows for multi-level treatment of the spine by providing either rigid fixation or dynamic stabilization at different levels to be treated is provided. This modular spine stabilization system may be configured to span multiple spine levels, and have a curvature that closely matches the curvature of the spine over those multiple levels to be treated. Further, the modular spine stabilization system allows adjustment of the curvature of the overall system such that the system may be adapted for a patient for a customized fit. Instruments are also provided for the assembly and/or implantation of the modular spine stabilization system. The associated instruments may include instruments for adjusting the curvature of the system to the patient, and for implanting the curved system into the patient. The instruments may be configured for implantation of the system in a minimally invasive surgery.

20 Claims, 23 Drawing Sheets

Related U.S. Application Data

(60) Provisional application No. 62/783,700, filed on Dec. 21, 2018, provisional application No. 62/783,541, filed on Dec. 21, 2018.

(56) References Cited

U.S. PATENT DOCUMENTS

| | | | |
|---|---|---|---|
| 5,672,175 | A | 9/1997 | Martin |
| 6,035,691 | A | 3/2000 | Lin et al. |
| 6,966,910 | B2 | 11/2005 | Ritland |
| 6,986,771 | B2 | 1/2006 | Paul et al. |
| 6,989,011 | B2 | 1/2006 | Paul et al. |
| 7,029,475 | B2 | 4/2006 | Panjabi |
| 7,137,985 | B2 | 11/2006 | Jahng |
| 7,291,150 | B2 | 11/2007 | Graf |
| 7,326,210 | B2 | 2/2008 | Jahng et al. |
| 7,329,258 | B2 | 2/2008 | Studer |
| 7,361,196 | B2 | 4/2008 | Fallin et al. |
| 7,377,921 | B2 | 5/2008 | Studer et al. |
| 7,476,238 | B2 | 1/2009 | Panjabi |
| 7,559,942 | B2 | 7/2009 | Paul et al. |
| 7,597,694 | B2 | 10/2009 | Lim et al. |
| 7,604,654 | B2 | 10/2009 | Fallin et al. |
| 7,615,068 | B2 | 11/2009 | Timm et al. |
| 7,621,912 | B2 | 11/2009 | Harms et al. |
| 7,621,940 | B2 | 11/2009 | Harms et al. |
| 7,625,393 | B2 | 12/2009 | Fallin et al. |
| 7,635,379 | B2 | 12/2009 | Callahan et al. |
| 7,641,673 | B2 | 1/2010 | Le Couedic et al. |
| 7,666,211 | B2 | 2/2010 | Perez-Cruet et al. |
| 7,682,375 | B2 | 3/2010 | Ritland |
| 7,713,287 | B2 | 5/2010 | Timm et al. |
| 7,717,941 | B2 | 5/2010 | Petit |
| 7,722,649 | B2 | 5/2010 | Biedermann et al. |
| 7,727,258 | B2 | 6/2010 | Graf |
| 7,727,259 | B2 | 6/2010 | Park |
| 7,763,048 | B2 | 7/2010 | Fortin et al. |
| 7,763,052 | B2 | 7/2010 | Jahng |
| 7,766,915 | B2 | 8/2010 | Jackson |
| 7,776,071 | B2 | 8/2010 | Fortin et al. |
| 7,785,350 | B2 | 8/2010 | Eckhardt et al. |
| 7,811,309 | B2 | 10/2010 | Timm et al. |
| 7,815,663 | B2 | 10/2010 | Trieu |
| 7,815,664 | B2 | 10/2010 | Sherman et al. |
| 7,815,665 | B2 | 10/2010 | Jahng et al. |
| 7,833,256 | B2 | 11/2010 | Biedermann et al. |
| 7,854,752 | B2 | 12/2010 | Colleran et al. |
| 7,862,586 | B2 | 1/2011 | Malek |
| 7,862,587 | B2 | 1/2011 | Jackson |
| 7,867,256 | B2 | 1/2011 | Schlaepfer |
| 7,875,059 | B2 | 1/2011 | Patterson et al. |
| 7,896,904 | B2 | 3/2011 | Perez-Cruet et al. |
| 7,927,356 | B2 | 4/2011 | Lim |
| 7,931,675 | B2 | 4/2011 | Panjabi et al. |
| 7,935,134 | B2 | 5/2011 | Reglos et al. |
| 7,942,905 | B2 | 5/2011 | Lim et al. |
| 7,951,170 | B2 | 5/2011 | Jackson |
| 7,988,707 | B2 | 8/2011 | Panjabi |
| 7,993,370 | B2 | 8/2011 | Jahng |
| 7,998,175 | B2 | 8/2011 | Kim |
| 8,012,177 | B2 | 9/2011 | Jackson |
| 8,012,178 | B2 | 9/2011 | Hartmann et al. |
| 8,012,179 | B2 | 9/2011 | Bruneau et al. |
| 8,012,180 | B2 | 9/2011 | Studer et al. |
| 8,025,680 | B2 | 9/2011 | Hayes et al. |
| 8,029,544 | B2 | 10/2011 | Hestad et al. |
| 8,029,548 | B2 | 10/2011 | Prevost et al. |
| 8,038,700 | B2 | 10/2011 | Colleran et al. |
| 8,043,339 | B2 | 10/2011 | Hudgins et al. |
| 8,043,340 | B1 | 10/2011 | Law |
| 8,048,132 | B2 | 11/2011 | Wu et al. |
| 8,057,516 | B2 | 11/2011 | Zylber et al. |
| 8,080,038 | B2 | 12/2011 | Bhatnagar et al. |
| 8,092,500 | B2 | 1/2012 | Jackson |
| 8,105,360 | B1 | 1/2012 | Connor |
| 8,105,368 | B2 | 1/2012 | Jackson |
| 8,109,973 | B2 | 2/2012 | Gerbec et al. |
| 8,118,840 | B2 | 2/2012 | Trieu et al. |
| 8,137,385 | B2 | 3/2012 | Gerbec et al. |
| 8,147,518 | B2 | 4/2012 | Brown et al. |
| 8,157,843 | B2 | 4/2012 | Biedermann et al. |
| 8,162,985 | B2 | 4/2012 | Kim |
| 8,172,880 | B2 | 5/2012 | Graf |
| 8,206,419 | B2 | 6/2012 | Marik et al. |
| 8,206,422 | B2 | 6/2012 | Hestad et al. |
| 8,216,280 | B2 | 7/2012 | White |
| 8,221,467 | B2 | 7/2012 | Butler et al. |
| 8,226,690 | B2 | 7/2012 | Altarac et al. |
| 8,231,657 | B2 | 7/2012 | Eckhardt et al. |
| 8,252,025 | B2 | 8/2012 | Viker |
| 8,267,967 | B2 | 9/2012 | McDonnell |
| 8,287,571 | B2 | 10/2012 | Semler et al. |
| 8,292,925 | B2 | 10/2012 | Hestad et al. |
| 8,292,926 | B2 | 10/2012 | Jackson |
| 8,292,927 | B2 | 10/2012 | Rouleau et al. |
| 8,308,770 | B2 | 11/2012 | Moumene et al. |
| 8,323,317 | B2 | 12/2012 | Hestad et al. |
| 8,333,790 | B2 | 12/2012 | Timm et al. |
| 8,337,526 | B2 | 12/2012 | Hestad et al. |
| 8,353,935 | B2 | 1/2013 | Krause |
| 8,353,936 | B2 | 1/2013 | Biedermann et al. |
| 8,361,118 | B2 | 1/2013 | Biedermann et al. |
| 8,366,745 | B2 | 2/2013 | Jackson |
| 8,372,116 | B2 | 2/2013 | Foley |
| 8,394,126 | B2 | 3/2013 | Biedermann et al. |
| 8,394,133 | B2 | 3/2013 | Jackson |
| 8,414,619 | B2 | 4/2013 | Trieu |
| 8,414,620 | B2 | 4/2013 | Sherman et al. |
| 8,425,562 | B2 | 4/2013 | Marik et al. |
| 8,425,565 | B2 | 4/2013 | Fallin et al. |
| 8,425,568 | B2 | 4/2013 | Bhatnagar et al. |
| 8,449,574 | B2 | 5/2013 | Biedermann et al. |
| 8,449,576 | B2 | 5/2013 | Lechmann et al. |
| 8,465,526 | B2 | 6/2013 | Friedrich et al. |
| 8,475,498 | B2 | 7/2013 | Jackson |
| 8,486,111 | B2 | 7/2013 | Ritland |
| 8,491,637 | B2 | 7/2013 | Matthis et al. |
| 8,491,638 | B2 | 7/2013 | Black |
| 8,500,781 | B2 | 8/2013 | Panjabi et al. |
| 8,506,599 | B2 | 8/2013 | Jackson |
| 8,518,084 | B2 | 8/2013 | Biedermann et al. |
| 8,529,603 | B2 | 9/2013 | Gerbec et al. |
| 8,535,351 | B1 | 9/2013 | Law |
| 8,562,652 | B2 | 10/2013 | Biedermann et al. |
| 8,585,739 | B2 | 11/2013 | Ritland |
| 8,591,560 | B2 | 11/2013 | Jackson |
| 8,613,760 | B2 | 12/2013 | Jackson |
| 8,617,215 | B2 | 12/2013 | Marik et al. |
| 8,623,057 | B2 | 1/2014 | Jahng et al. |
| 8,623,058 | B2 | 1/2014 | Hestad et al. |
| 8,623,059 | B2 | 1/2014 | Gerbec et al. |
| 8,632,570 | B2 | 1/2014 | Biedermann et al. |
| 8,641,734 | B2 | 2/2014 | Moumene et al. |
| 8,652,175 | B2 | 2/2014 | Timm et al. |
| 8,663,284 | B2 | 3/2014 | Beger et al. |
| 8,668,720 | B2 | 3/2014 | Perez-Cruet et al. |
| 8,685,062 | B2 | 4/2014 | Ritland |
| 8,690,922 | B2 | 4/2014 | Ritland |
| 8,709,048 | B2 | 4/2014 | Cheng et al. |
| 8,740,944 | B2 | 6/2014 | Trieu et al. |
| 8,740,945 | B2 | 6/2014 | Hestad et al. |
| 8,795,336 | B2 | 8/2014 | Biedermann et al. |
| 8,858,600 | B2 | 10/2014 | Brown et al. |
| 8,888,817 | B2 | 11/2014 | Sherman et al. |
| 8,920,473 | B2 | 12/2014 | Trautwein et al. |
| 8,932,334 | B2 | 1/2015 | Ritland |
| 8,968,366 | B2 | 3/2015 | Jahng |
| 8,974,497 | B2 | 3/2015 | Cho et al. |
| 8,974,498 | B2 | 3/2015 | Beger et al. |
| 8,974,499 | B2 | 3/2015 | Fallin et al. |
| 8,979,900 | B2 | 3/2015 | Jahng et al. |
| 8,992,577 | B2 | 3/2015 | Cheng et al. |
| 9,005,252 | B2 | 4/2015 | Panjabi et al. |
| 9,011,494 | B2 | 4/2015 | Trieu |

(56) References Cited

U.S. PATENT DOCUMENTS

| | | |
|---|---|---|
| 9,017,385 B1 | 4/2015 | Law |
| 9,034,016 B2 | 5/2015 | Panjabi |
| 9,034,018 B2 | 5/2015 | Zylber et al. |
| 9,050,140 B2 | 6/2015 | Semler et al. |
| 9,072,544 B2 | 7/2015 | Fortin et al. |
| 9,072,545 B2 | 7/2015 | Biedermann et al. |
| 9,072,546 B2 | 7/2015 | Trieu et al. |
| 9,078,704 B2 | 7/2015 | Beger et al. |
| 9,089,369 B2 | 7/2015 | Biedermann et al. |
| 9,119,672 B2 | 9/2015 | Prevost et al. |
| 9,138,263 B2 | 9/2015 | Krause |
| 9,144,439 B2 | 9/2015 | Trieu |
| 9,147,976 B2 | 9/2015 | Ao et al. |
| 9,155,580 B2 | 10/2015 | Cormier et al. |
| 9,211,142 B2 | 12/2015 | Friedrich et al. |
| 9,220,538 B2 | 12/2015 | Friedrich et al. |
| 9,232,967 B2 | 1/2016 | Ritland |
| 9,232,968 B2 | 1/2016 | Moumene et al. |
| 9,333,008 B2 | 5/2016 | Dodgen et al. |
| 9,339,297 B2 | 5/2016 | Friedrich et al. |
| 9,445,844 B2 | 9/2016 | Moumene et al. |
| 9,445,845 B2 | 9/2016 | Bhatnagar et al. |
| 9,445,846 B2 | 9/2016 | Gerbec et al. |
| 9,486,244 B2 | 11/2016 | Fallin et al. |
| 9,492,202 B2 | 11/2016 | Matthis et al. |
| 9,522,018 B2 | 12/2016 | Trautwein et al. |
| 9,532,808 B2 | 1/2017 | Celmerowski et al. |
| 9,636,145 B2 | 5/2017 | Friedrich et al. |
| 9,642,651 B2 | 5/2017 | Bowden et al. |
| 9,655,651 B2 | 5/2017 | Panjabi |
| 9,681,893 B2 | 6/2017 | Panjabi et al. |
| 9,730,733 B2 | 8/2017 | Cho et al. |
| 9,737,339 B2 | 8/2017 | Copp et al. |
| 10,004,539 B2 | 6/2018 | Gerbec et al. |
| 2002/0161368 A1 | 10/2002 | Foley et al. |
| 2003/0171749 A1 | 9/2003 | Le Couedic et al. |
| 2005/0065516 A1 | 3/2005 | Jahng |
| 2005/0131407 A1 | 6/2005 | Sicvol et al. |
| 2005/0143737 A1 | 6/2005 | Pafford et al. |
| 2005/0149020 A1 | 7/2005 | Jahng |
| 2005/0154390 A1* | 7/2005 | Biedermann ...... A61B 17/7028 606/279 |
| 2005/0171543 A1 | 8/2005 | Timm et al. |
| 2005/0177164 A1 | 8/2005 | Walters et al. |
| 2005/0182400 A1 | 8/2005 | White |
| 2005/0182401 A1 | 8/2005 | Timm et al. |
| 2005/0203513 A1 | 9/2005 | Jahng et al. |
| 2006/0150699 A1 | 7/2006 | Garner et al. |
| 2006/0184171 A1 | 8/2006 | Biedermann et al. |
| 2006/0212033 A1 | 9/2006 | Rothman et al. |
| 2006/0229608 A1 | 10/2006 | Foster et al. |
| 2007/0088359 A1* | 4/2007 | Woods ............... A61B 17/7049 606/86 A |
| 2007/0270838 A1 | 11/2007 | Bruneau et al. |
| 2007/0288009 A1 | 12/2007 | Brown et al. |
| 2008/0045951 A1* | 2/2008 | Fanger ................ A61B 17/705 606/86 A |
| 2008/0161853 A1 | 7/2008 | Arnold et al. |
| 2008/0161863 A1 | 7/2008 | Arnold et al. |
| 2008/0172091 A1 | 7/2008 | Anderson |
| 2008/0177316 A1 | 7/2008 | Bergeron et al. |
| 2008/0262554 A1 | 10/2008 | Hayes et al. |
| 2009/0030465 A1 | 1/2009 | Altarac et al. |
| 2009/0048631 A1* | 2/2009 | Bhatnagar .......... A61B 17/7004 606/264 |
| 2009/0088782 A1 | 4/2009 | Moumene et al. |
| 2009/0093846 A1 | 4/2009 | Hestad |
| 2009/0099606 A1 | 4/2009 | Hestad et al. |
| 2009/0099608 A1 | 4/2009 | Szczesny |
| 2009/0163953 A1* | 6/2009 | Biedermann ........ A61B 17/705 606/260 |
| 2009/0182378 A1 | 7/2009 | Choi |
| 2009/0198291 A1* | 8/2009 | Kevin ................ A61B 17/863 606/301 |
| 2009/0228045 A1 | 9/2009 | Hayes et al. |
| 2009/0234388 A1 | 9/2009 | Patterson et al. |
| 2009/0240284 A1 | 9/2009 | Randol et al. |
| 2009/0248081 A1 | 10/2009 | Ehuec et al. |
| 2009/0248083 A1 | 10/2009 | Patterson et al. |
| 2009/0259257 A1 | 10/2009 | Prevost |
| 2009/0326583 A1 | 12/2009 | Moumene et al. |
| 2009/0326584 A1 | 12/2009 | Slivka et al. |
| 2010/0069962 A1 | 3/2010 | Harms et al. |
| 2010/0114169 A1 | 5/2010 | Le Couedic et al. |
| 2010/0114173 A1 | 5/2010 | Le Couedic et al. |
| 2010/0160968 A1 | 6/2010 | Joshi et al. |
| 2010/0204736 A1 | 8/2010 | Biedermann et al. |
| 2010/0222820 A1 | 9/2010 | Trieu |
| 2010/0228292 A1 | 9/2010 | Arnold et al. |
| 2010/0318130 A1 | 12/2010 | Parlato et al. |
| 2011/0009906 A1 | 1/2011 | Hestad et al. |
| 2011/0040331 A1 | 2/2011 | Fernandez et al. |
| 2011/0046676 A1 | 2/2011 | Droulout et al. |
| 2011/0112579 A1 | 5/2011 | Brazil et al. |
| 2011/0137346 A1 | 6/2011 | Overes et al. |
| 2011/0152948 A1* | 6/2011 | Crook ................ A61B 17/7037 606/305 |
| 2011/0184467 A1 | 7/2011 | Lim |
| 2011/0245871 A1 | 10/2011 | Williams |
| 2011/0307016 A1 | 12/2011 | Reglos et al. |
| 2012/0209330 A1 | 8/2012 | Jahng et al. |
| 2012/0265247 A1 | 10/2012 | Biedermann et al. |
| 2013/0110169 A1 | 5/2013 | Hynes et al. |
| 2014/0012334 A1* | 1/2014 | Armstrong .......... A61B 17/863 606/312 |
| 2014/0031868 A1 | 1/2014 | Biedermann et al. |
| 2014/0066986 A1 | 3/2014 | Biedermann et al. |
| 2014/0121703 A1* | 5/2014 | Jackson ............. A61B 17/7032 606/246 |
| 2014/0137618 A1 | 5/2014 | Isaacs |
| 2014/0200615 A1 | 7/2014 | Yeh |
| 2014/0379031 A1 | 12/2014 | Biedermann et al. |
| 2015/0201970 A1 | 7/2015 | Aferzon |
| 2015/0289916 A1* | 10/2015 | Sharps ............... A61B 17/7032 606/315 |
| 2016/0120577 A1 | 5/2016 | Friedrich et al. |
| 2017/0056073 A1 | 3/2017 | Celmerowski et al. |
| 2017/0095274 A1 | 4/2017 | Trautwein et al. |
| 2017/0135730 A1 | 5/2017 | Sauvage et al. |
| 2018/0014863 A1* | 1/2018 | Biester ............... A61B 17/7001 |
| 2018/0206896 A1 | 7/2018 | Yoon et al. |
| 2018/0303524 A1 | 10/2018 | Iott et al. |
| 2019/0223917 A1* | 7/2019 | Gray ................. A61B 17/7082 |

FOREIGN PATENT DOCUMENTS

| | | |
|---|---|---|
| EP | 2142121 B1 | 4/2014 |
| EP | 3085320 A1 | 2/2016 |
| EP | 2979653 B1 | 4/2017 |
| WO | 2006063107 A2 | 6/2006 |
| WO | 2006096241 A2 | 9/2006 |
| WO | 2006096414 A1 | 9/2006 |
| WO | 2007136612 A2 | 11/2007 |
| WO | 2007145706 A2 | 12/2007 |
| WO | 2008013892 A2 | 1/2008 |
| WO | 2008134703 A2 | 11/2008 |
| WO | 2008157589 A1 | 12/2008 |
| WO | 2009021116 A2 | 2/2009 |
| WO | 2009042489 A2 | 4/2009 |
| WO | 2010014174 A1 | 2/2010 |
| WO | 2012022047 A1 | 2/2012 |
| WO | 2012024807 A1 | 3/2012 |
| WO | 2014012491 A1 | 1/2014 |
| WO | 2014015756 A1 | 1/2014 |
| WO | 2015062408 A1 | 5/2015 |

(56) References Cited

FOREIGN PATENT DOCUMENTS

| WO | WO 2015/195843 | 12/2015 |
| WO | WO 2020/132571 | 6/2020 |

OTHER PUBLICATIONS

International Preliminary Report on Patentability for International (PCT) Patent Application No. PCT/US2019/068059, dated Jul. 1, 2021, 9 pages.
Extended European Search Report for Europe Patent Application No. 19898271.2, dated Aug. 29, 2022, 10 pages.
Official Action for U.S. Appl. No. 16/723,072, dated Jun. 21, 2021, 12 pages.
Official Action for U.S. Appl. No. 16/723,072, dated Dec. 10, 2021, 13 pages.
Notice of Allowance for U.S. Appl. No. 16/723,072, dated Jun. 30, 2022, 7 pages.
Notice of Allowance for U.S. Appl. No. 16/723,072, dated Oct. 26, 2022, 5 pages.

* cited by examiner

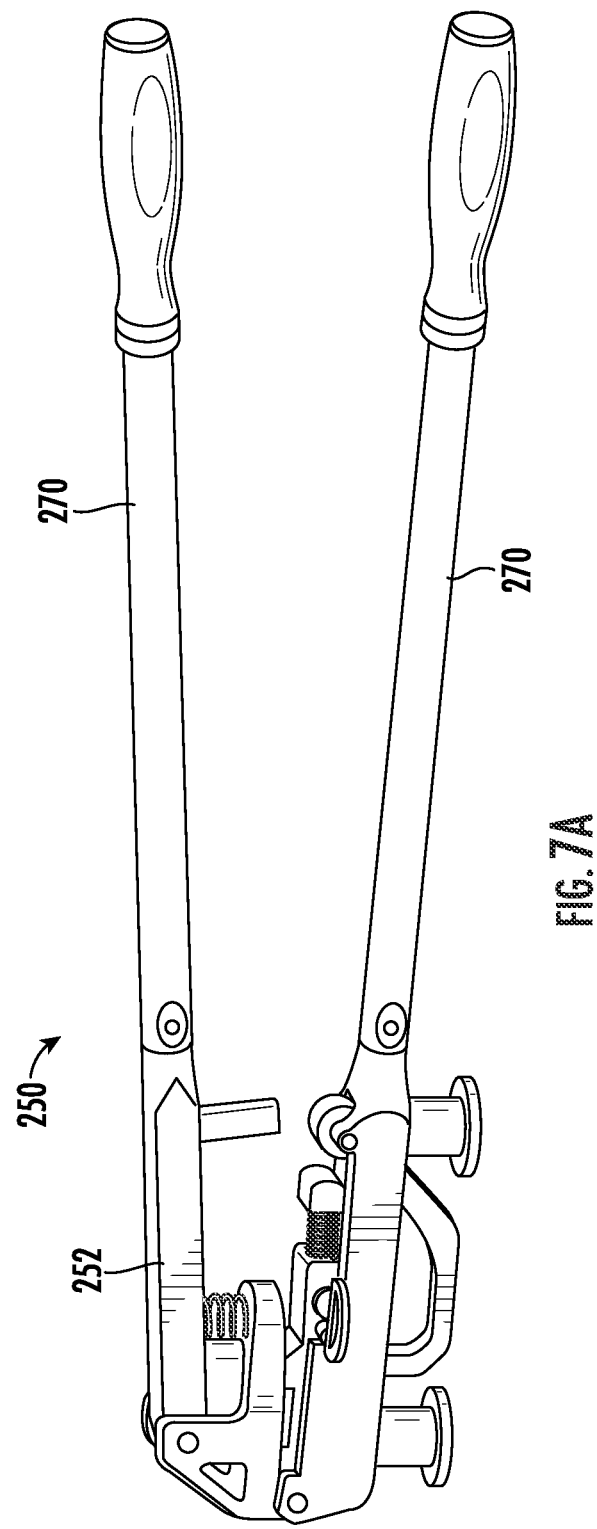

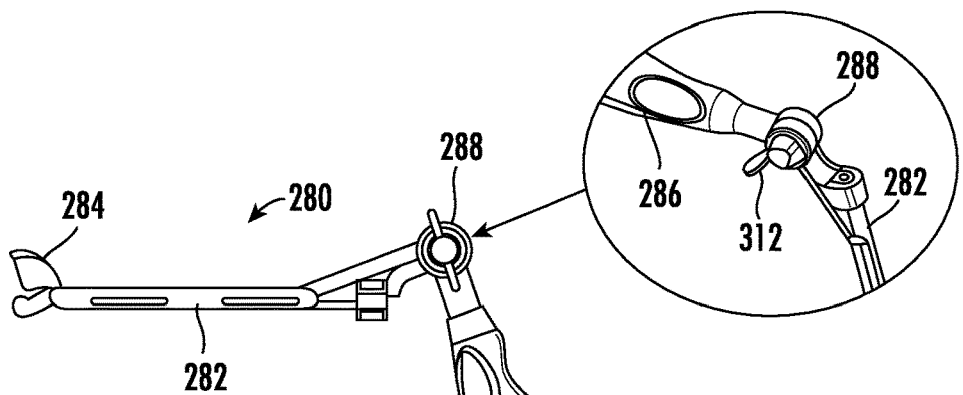
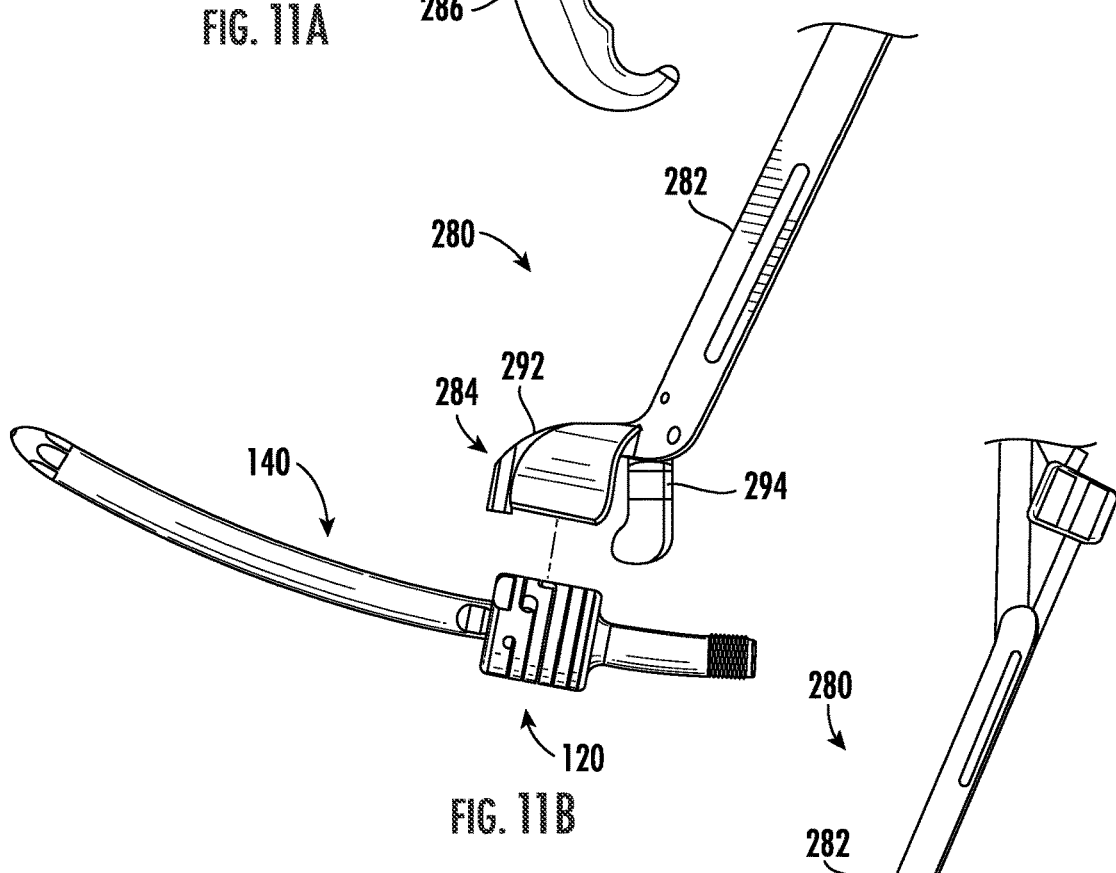
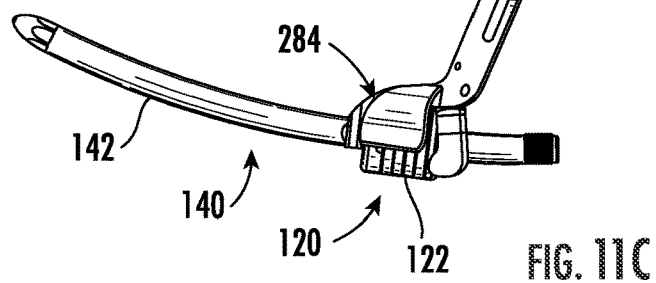

MODULAR SPINE STABILIZATION SYSTEM AND ASSOCIATED INSTRUMENTS

CROSS-REFERENCE TO RELATED APPLICATIONS

This application is a continuation of U.S. patent application Ser. No. 16/723,072, filed Dec. 20, 2019, which claims the benefit of U.S. Provisional Application No. 62/783,700, filed Dec. 21, 2018 and U.S. Provisional Application No. 62/783,541, filed Dec. 21, 2018, the entire contents of which are herein incorporated in their entirety by reference.

FIELD

The present disclosure generally relates to medical devices for the treatment of spinal conditions, and specifically to an implantable, modular spine stabilization system for controlling or restricting relative motion between vertebrae Instruments for the assembly and/or implantation of such a modular spine stabilization system are also provided.

BACKGROUND

The spine includes a series of joints known as motion segment units. Each unit represents the smallest component of the spine to exhibit a kinematic behavior characteristic of the entire spine. The motion segment unit is capable of flexion, extension, lateral bending, and translation. The components of each motion segment unit include two adjacent vertebrae, the corresponding apophyseal joints, an intervertebral disc, and connecting ligamentous tissue, with each component of the motion segment unit contributing to the mechanical stability of the joint. For example, the intervertebral discs that separate adjacent vertebrae provide stiffness that helps to restrain relative motion of the vertebrae in flexion, extension, axial rotation, and lateral bending.

When the components of a motion segment unit move out of position or become damaged due to trauma, mechanical injury or disease, severe pain and further destabilizing injury to other components of the spine may result. In a patient with degenerative disc disease (DDD), a damaged disc may provide inadequate stiffness, which may result in excessive relative vertebral motion when the spine is under a given load, causing pain and further damage to the disc. Depending upon the severity of the structural changes that occur, treatment may include fusion, discectomy, and/or a laminectomy.

Known treatments for spinal instability can include long-term medical management or surgery. Medical management is generally directed at controlling the symptoms, such as pain reduction, rather than correcting the underlying problem. For some patients, this may require chronic use of pain medications, which may alter the patient's mental state or cause other negative side effects. Surgical treatment typically includes decompression procedures to restore normal disc height, realign the column, and alleviate the pain.

Current surgical treatments often involve the immobilization or fusion of unstable motion segment units, sometimes with the removal of adjacent tissue. One such treatment method involves the rigid fixation of the spine at one or more levels by securing a rigid rod against the spine to prevent motion and thereby enable fusion.

An alternative surgical treatment also stabilizes the spine, but preserves motion instead of promoting fusion. This type of dynamic stabilization typically involves the fixation of a dynamic or spring-like coupler between vertebrae, which would still serve to stabilize and limit motion of the spine, but also allow close-to-normal motion, mimicking the physiological response of a healthy motion segment and providing pain relief, at that level.

There is, nevertheless, a need for a surgical treatment that can address multi-level spine stabilization, and an implantable, modular spine stabilization system that can achieve one or the other type of stabilization at different levels. Rather than having different or separate rod systems to treat multiple levels of the same spine by either rigidly fixing or dynamically stabilizing a single level, what would be desirable is a modular spine stabilization system that could allow either rigid fixation or dynamic stabilization at each level of the same spine to be treated. Further, since this spine stabilization system would span multiple spine levels, it would be further desirable to enable the system to have a curvature that closely matches the curvature of the spine over those multiple levels to be treated, and even more desirable to be able to adjust the curvature of the system to the patient for a customized fit. Accordingly, associated instruments for the assembly and/or implantation of such a modular spine stabilization system are also desirable.

SUMMARY

The present disclosure provides an implantable, modular spine stabilization system that allows for multi-level treatment of the spine by providing either rigid fixation or dynamic stabilization at different levels to be treated. This modular spine stabilization system may be configured to span multiple spine levels, and have a curvature that closely matches the curvature of the spine over those multiple levels to be treated. Further, the modular spine stabilization system allows adjustment of the curvature of the overall system such that the system may be adapted for a patient for a customized fit.

Instruments are also provided for the assembly and/or implantation of the modular spine stabilization system. The associated instruments may include instruments for adjusting the curvature of the system to the patient, and for implanting the curved system into the patient. The instruments may be configured for implantation of the system in a minimally invasive surgery. Methods for stabilizing a spine using the implantable, modular spine stabilization system and the associated instruments for assembly and implantation are also provided.

In one exemplary embodiment, a kit for modular spine stabilization is provided. The kit may comprise an implantable modular spine stabilization system and an associated instrument set for use with the implantable modular spine stabilization system. The spine stabilization system may comprise one or more flexible couplers for dynamic stabilization of a spinal segment of a patient's spine. Each coupler may have a stem. The system may further comprise one or more rigid rods for rigid stabilization of a spinal segment of the patient's spine. Each rigid rod may have an elongated shaft. One or more bone fasteners for attaching the flexible couplers or rigid rods to a patient's spine are also provided in the system.

An instrument set for attaching the spine stabilization system to the patient's spine may also be provided with the kit. The instrument set may include a bending instrument for bending a stem of one of the flexible couplers.

In some embodiments, a flexible coupler may be configured to attach to one or more flexible couplers. In other embodiments, a flexible coupler may be configured to attach to a rigid rod.

The stem of the flexible coupler may be curved, or the stem may be straight. Likewise, the shaft of the rigid rod may be curved, or it may be straight. The stem of the flexible coupler may be bendable. The stem and shaft of the flexible coupler and rigid rod, respectively, have threaded ends while the flexible coupler comprises a body having a threaded opening, so that these components can be threadedly connected in series to one another.

The one or more flexible couplers may be provided as a set, and may be differently sized. Likewise, the rigid rods may be provided as a set, and may be differently sized.

In one exemplary embodiment, the bending instrument may comprise a base having a pivoting arm, a pivoting rod holder, and a radius of curvature selection wheel. The pivoting arm may have a pusher bar and a pusher head extending from a lower surface therefrom. The pivoting rod holder may have a portal for receiving a rod of a medical device to be bent. The bending instrument may be configured such that the lowering of the pivoting arm causes the pusher bar to press against the radius of curvature selection wheel and the pusher head to press against the rod held within the pivoting rod holder.

The pivoting arm can include a handle attachment end. Likewise, the base can also include a handle attachment end. The radius of curvature selection wheel includes one or more detents corresponding to a different radius of curvature. In addition, the pivoting arm can attach to the base at a pivoting hinge.

The pivoting rod holder can include a portal, which may be threaded, for receiving the rod of the medical device. The bending instrument may also include a damper between the pivoting arm and the base. The bending instrument may also include detachable handles for attachment to the base and arm.

As previously mentioned, the bending instrument may be used for bending rods of medical devices. In particular, the bending instrument may be used to bend a stem of the medical device. The medical device may be a flexible coupler such as the one provided in the modular spine stabilization system of the present disclosure.

Other instruments provided with the instrument set of the present disclosure may include a flexible coupler and rod inserter tool. The flexible coupler and rod inserter tool may include an angularly adjustable neck, and be configured for use in a minimally invasive surgery.

Another instrument that may be provided with the instrument set of the present disclosure includes a contouring template. Still another instrument may include a flexible coupler and rigid rod clamping instrument configured to clamp onto a guide rod, which may also be provided with the instrument set of the present disclosure.

The modular spine stabilization system of the present disclosure may include bone fasteners. The bone fastener may comprise a head portion and a shank portion. The head portion may include a cavity for receiving an implantable device. The shank portion may include an elongated shaft extending to a distal tip. The shank portion may have an enlarged head captured within the cavity of the head portion and being defined by a first leading threaded portion adjacent the distal tip. The shank portion may be defined by a first leading threaded portion adjacent the distal tip, a second trailing threaded portion adjacent the head portion, and an intermediate threaded portion extending between the first and second threaded portions. In one exemplary embodiment, the implantable device may comprise a rod.

In one embodiment, the first leading threaded portion includes quad lead threads and the second trailing threaded portion may include quad lead threads. In some embodiments, the shank portion may have a generally uniform diameter from the second trailing threaded portion to the end of the intermediate threaded portion, while the first leading threaded portion may have a conical shape. In some embodiments, the first leading threaded portion may include cutting notches. The bone fastener may be cannulated and include cement holes for use with bone cement, in some embodiments.

Additionally, the bone fastener may be color coded for different sizes, and may be configured with a self-tapping distal tip. A locking device for securing the implantable device within the cavity may be provided, in which the locking device is a set screw. Further, the head portion may be attached to an extended head portion at a scored region. This extended head portion may be configured to break away from the head region after use. Additionally, the bone fastener may include an elongate head region for use in a minimally invasive surgery. Once the assembly process is completed, this elongate head region may be snapped off.

The present disclosure may also provide an implantable, modular spine stabilization system. This system may include one or more flexible couplers for dynamic stabilization of a spinal segment of a patient's spine. Each flexible coupler may have a flexible main body and a bendable stem extending therefrom. The system may also include one or more rigid rods for rigid stabilization of a spinal segment of the patient's spine. Each rigid rod may have an elongated shaft.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIGS. 4A to 4F illustrate various configurations of the modular spine stabilization system of the present disclosure, in which:

FIG. 4A is an exploded view of a system configuration comprising a flexible coupler with a straight stem and a curved rod;

FIG. 4B is a perspective view of a system configuration comprising a flexible coupler with a curved stem attached to a curved rod;

FIG. 4C is a perspective view of a system configuration comprising a flexible coupler with a straight stem attached to a straight rod;

FIG. 4D is a perspective view of a system configuration comprising a flexible coupler with a curved stem attached to a curved rod;

FIG. 4E is perspective view of a system configuration comprising two flexible couplers and a rod, and all of which have curved stems or shafts, for attachment in series together; and FIG. 4F is a perspective view of a system configuration comprising two flexible couplers and a rod, all of which have straight stems or shafts.

FIG. 7A is a perspective view of an exemplary embodiment of a bending instrument of the present disclosure for bending a stem of a flexible coupler, attached to detachable handles.

FIGS. 8A to 8H illustrate a method for bending a stem of a flexible coupler using the bending instrument of FIGS. 7A and 7B, in which:

FIG. 8A shows the bending instrument in an open position with the arm raised;

FIG. 8B shows the flexible coupler mounting unit swiveled upward on the bending instrument;

FIG. 8C shows the selected flexible coupler inserted into the flexible coupler mounting unit of the bending instrument, including an enlarged view;

FIG. 8D shows the flexible coupler mounting unit swiveled back to reside within the base of the bending instrument and the correct radius chosen, including an enlarged view;

FIG. 8E is a partial cutaway view of the bending instrument in a partially closed position with the arm lowered.

FIG. 8F is a partial cutaway view of the bending instrument in a fully closed position with the arm fully lowered;

FIG. 8G shows the bending instrument in an open position, with the flexible coupler mounting unit swiveled upward, including an enlarged view; and FIG. 8H shows the flexible coupler with a bent stem being removed from the bending instrument.

FIGS. 11A to 11C are perspective views of an exemplary embodiment of a flexible coupler and rod inserter tool of the present disclosure, in which:

FIG. 11A illustrates a perspective view of the inserter tool;

FIG. 11B shows a method of using the inserter tool to grasp a flexible coupler of the system of FIG. 1; and FIG. 11C shows the inserter tool in use with a flexible coupler of the system of FIG. 1.

FIGS. 12A to 12E illustrate an exemplary method of using the inserter tool of FIGS. 11A to 11C, in which:

FIG. 12A illustrates an exemplary surgical guide for making incisions to access the patient's spine; and FIGS. 12C to 12E show a method of using the inserter tool to introduce a flexible coupler and rod construct into the patient's spine.

DETAILED DESCRIPTION OF THE EMBODIMENTS

This description and the accompanying drawings illustrate exemplary embodiments and should not be taken as limiting, with the claims defining the scope of the present disclosure, including equivalents. Various mechanical, compositional, structural, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment. Moreover, the depictions herein are for illustrative purposes only and do not necessarily reflect the actual shape, size, or dimensions of the system or illustrated components.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

The present disclosure provides an implantable, modular spine stabilization system that allows for multi-level treatment of the spine by providing either rigid fixation or dynamic stabilization at different levels to be treated. This modular spine stabilization system may be configured to span multiple spine levels, and have a curvature that closely matches the curvature of the spine over those multiple levels to be treated. Further, the modular spine stabilization system allows adjustment of the curvature of the overall system such that the system may be adapted for a patient for a customized fit.

Instruments are also provided for the assembly and/or implantation of the modular spine stabilization system. The associated instruments may include instruments for adjusting the curvature of the system to the patient, and for implanting the curved system into the patient. The instruments may be configured for implantation of the system in a minimally invasive surgery.

Figure 1:
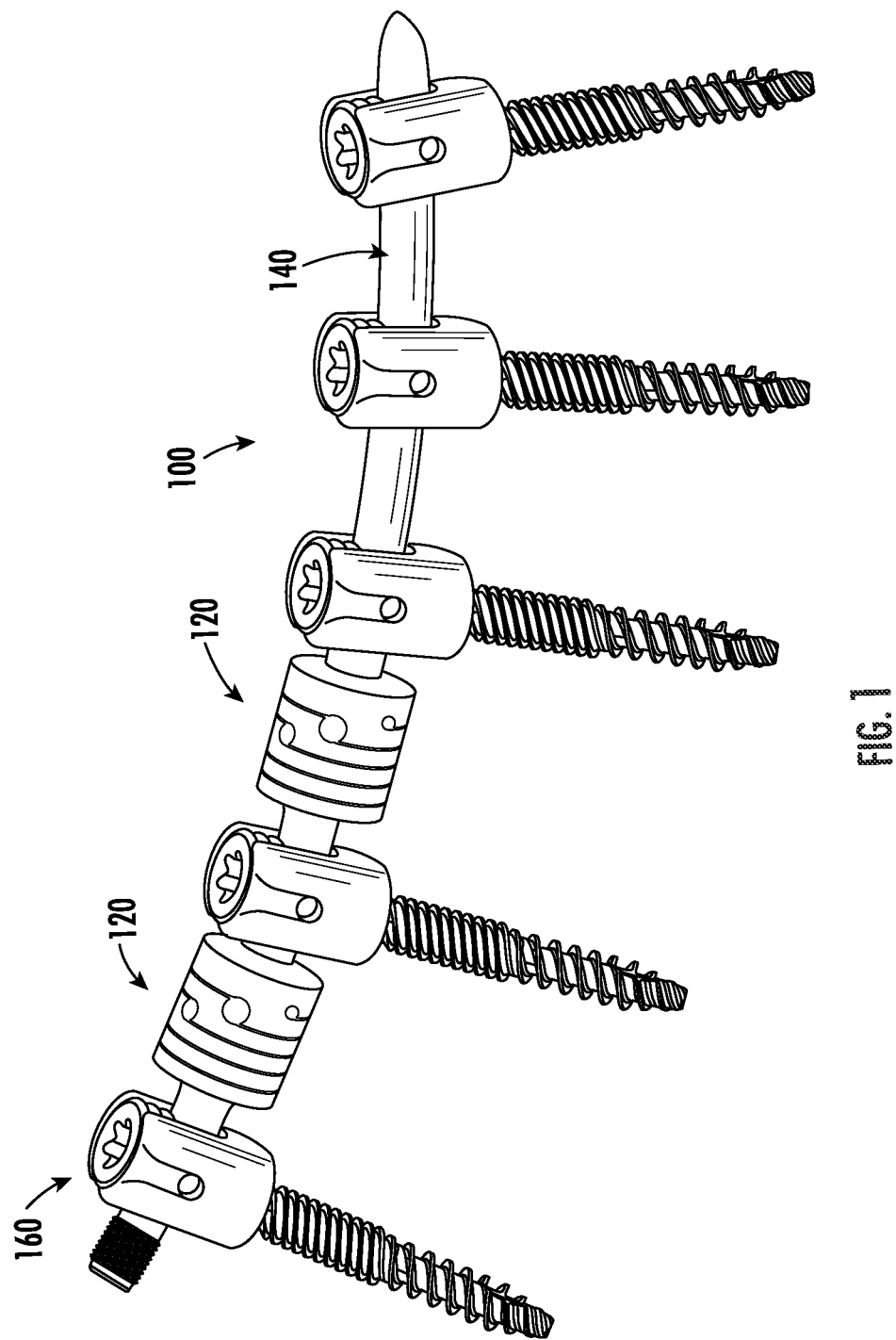
FIG. 1 is a perspective view of an exemplary embodiment of a modular spine stabilization system of the present disclosure.

Turning now to the drawings, FIG. 1 illustrates an exemplary embodiment of a modular spine stabilization system 100 of the present disclosure. The system 100 may be configured for multi-level treatment of the spine, with different, individual levels being either rigidly fixed or dynamically stabilized. As shown, a pair of implantable flexible couplers 120 may be connected in series, along with an implantable rigid rod 140, to enable multi-level spine stabilization with varied degrees of fixation at individual levels. Bone fasteners 160 may be used to secure the couplers 120 and the rigid rod 140 to the spine. These flexible couplers 120 allow limited motion at that level where they are positioned, while the rigid rod 140 provides rigid fixation where it is connected.

Figure 2A:
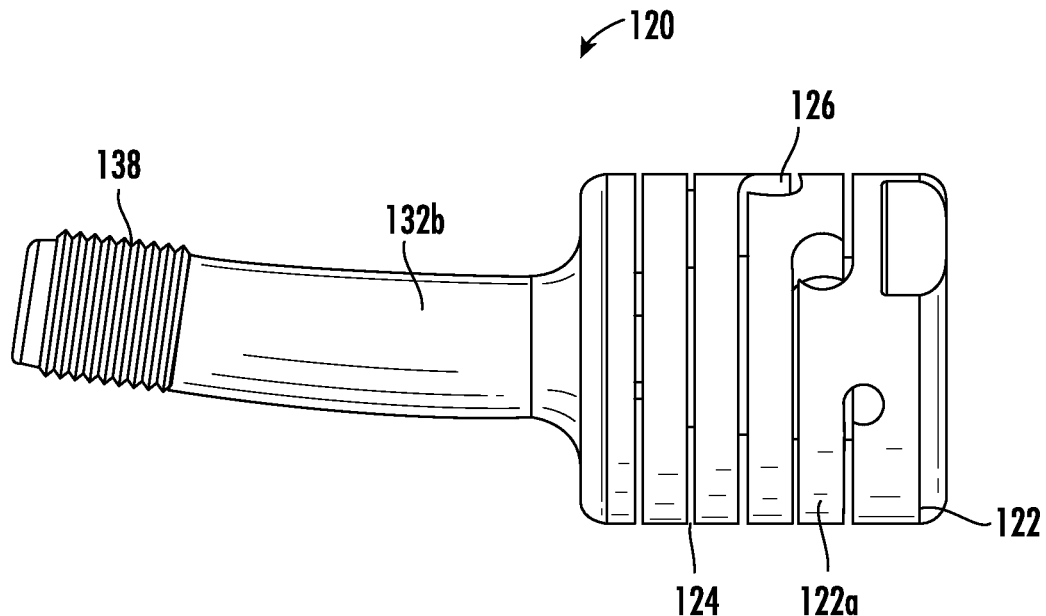
FIG. 2A is a perspective view of an exemplary embodiment of a flexible coupler of the present disclosure having a curved stem.
Figure 2B:
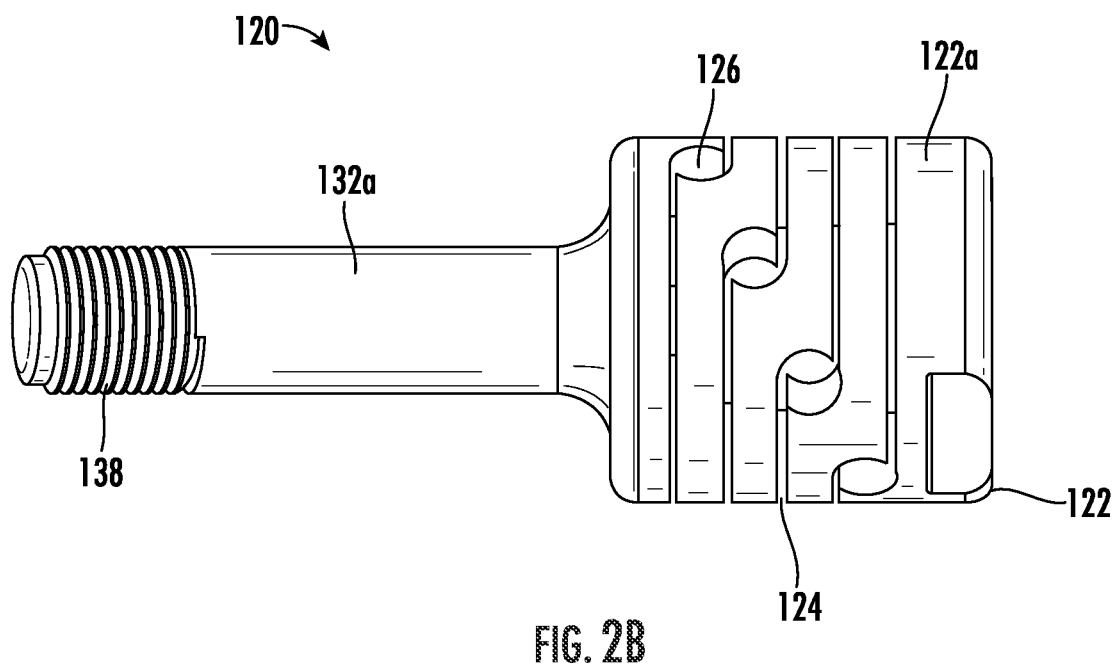
FIG. 2B is a perspective view of an exemplary embodiment of a flexible coupler of the present disclosure having a straight stem.
Figure 2C:
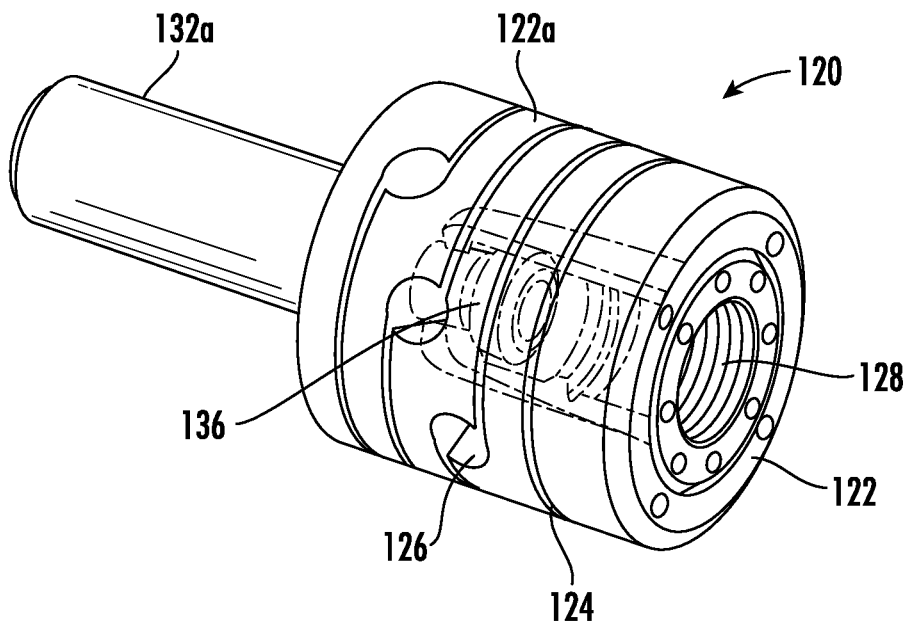
FIG. 2C is a partial cutaway view of the flexible coupler of FIG. 2B showing an internal range-of-motion limiting mechanism.

The modular spine stabilization system 100 of the present disclosure may provide two different types of flexible couplers for dynamic stabilization of a spine level: FIG. 2A shows an exemplary embodiment of a flexible coupler 120 having a curved or angled stem 132b, while FIG. 2B shows an exemplary embodiment of a flexible coupler 120 having a straight stem 132a. Each of the stems 132a, 132b may include a threaded end 138, as shown. The flexible coupler 120 may be similar to the flexible coupler described in U.S. Pat. Nos. 10,092,329, 9,522,018, and 8,920,473, the contents of all of which are herein incorporated in their entirety by reference. Accordingly, as shown, the flexible coupler 120 may comprise a main body 122 such as the cylindrical body shown in FIGS. 2A to 2C. The flexible coupler body 122 may be flexible, compressible, and/or extendable, and formed from a series of coil units 122a. The series of coil units 122a may be connected to one another to form a stepwise series of slots 124. Each slot 124 terminates at an opening 126 of the flexible body 122. A threaded opening 128 may be provided on the flexible body 122, as shown in FIG. 2C. If so desired, the flexible coupler body 122 may comprise an internal distraction-compression stopping mechanism to control or limit the range of motion that can be offered. For example, as shown in FIG. 2C, a range-of-motion limiting mechanism 136 may be provided within the flexible coupler body 122. The internal distraction-compression stopping mechanism 136 may be similar to the one described in the aforementioned patents.

In some embodiments, the series of coil units 122A can be formed from a single piece of material such that the units 122A are integrally connected with one another. For example, in one embodiment, the coil units 122A can be etched or cut from a single, tubular piece of material. In other embodiments, one or more coil units 122A can be formed individually and stacked upon one another. The stacked coil units 122A can be connected to one another, for example, by welding or through mechanical connections.

It is contemplated that the flexible coupler body 122 may vary in degree of stiffness based on the height, width, distance or angle between two adjacent slots 124 and the number of units 122A forming the coupler body 122. Further, one or more units 122A may be formed from different materials so as to vary the mechanical properties of the body 122. In addition, the dimensions of the units 122A, slots 124, and openings 126 can be varied within a single body 122.

Figure 3A:
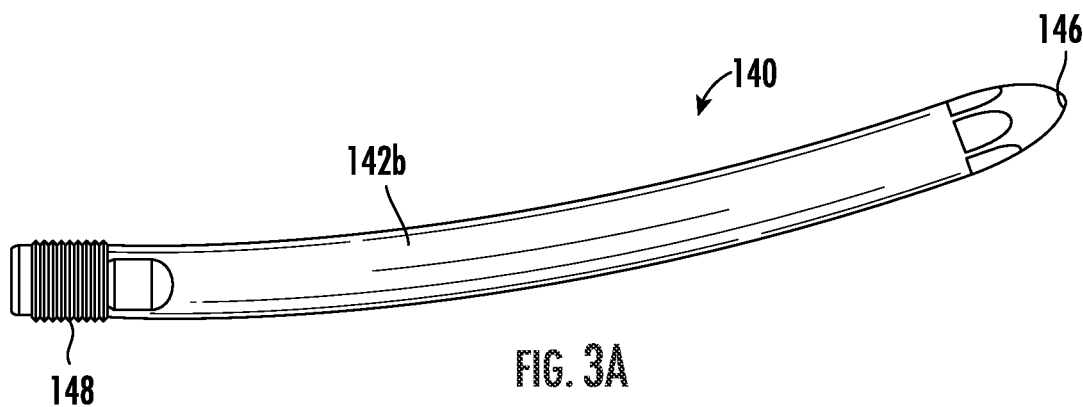
FIG. 3A is a perspective view of an exemplary embodiment of a rigid rod of the present disclosure having a curved shaft.
Figure 3B:
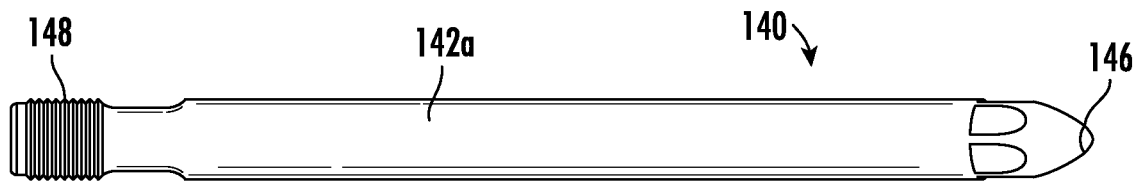
FIG. 3B is a perspective view of an exemplary embodiment of a rigid rod of the present disclosure having a straight shaft.

The modular spine stabilization system 100 of the present disclosure may also provide two different types of rigid rods for rigid fixation of a spine level: FIG. 3A shows a rigid rod 140 having a curved or angled shaft 142b, while FIG. 3B shows a rigid rod 140 having a straight shaft 142a. Each of the shafts 142a, 142b may have a tapered, blunt end 146 and an opposed, threaded end 148, as shown.

It is understood that each of these flexible couplers 120 or rigid fixation rods 140 may be provided in various sizes (e.g., length, diameter, angle of stem).

Figure 4A:
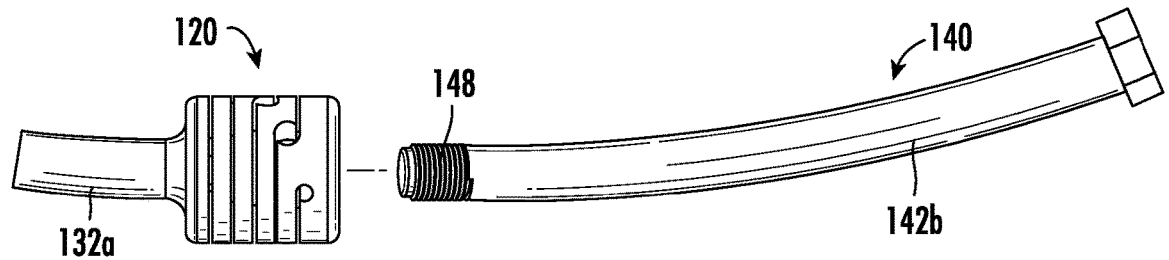
Figure 4B:
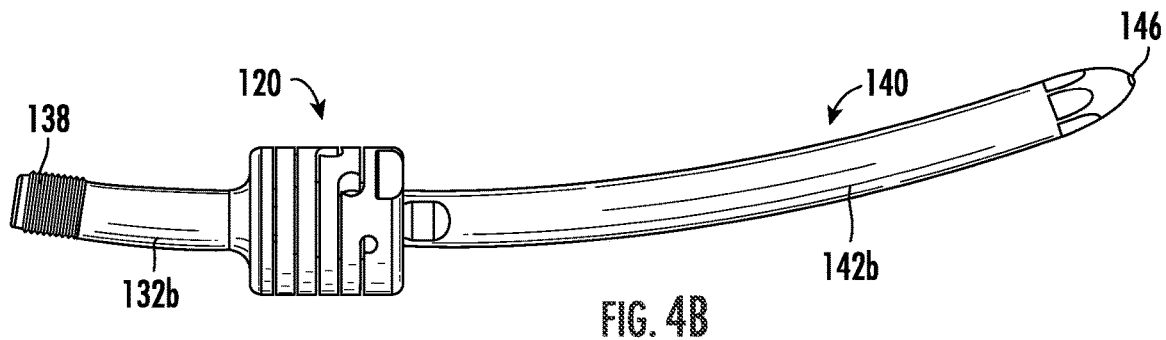

One of the advantages of the modular spine stabilization system 100 of the present disclosure is that it is customizable, and allows the user to selective choose which type of flexible coupler 120 and/or which type of rigid rod 140 to attach in series together, depending on the level of rigidity required at that spinal level, as well as the curvature of the spine to be stabilized. This modularity provides the surgeon with ultimate flexibility in customizing the multi-level spine stabilization system to the patient's needs. For example, FIGS. 4A to 4F show the various modular constructs, or configurations, in which this modular spine stabilization system 100 may be assembled and utilized:

FIG. 4A shows a system configuration, or construct, comprising a flexible coupler 120 with a straight stem 132a to be attached to a rigid rod 140 having a curved shaft 142b, while FIG. 4B shows a system configuration, or construct, comprising a flexible coupler 120 with a curved stem 132b attached to a rigid rod 140 having a curved shaft 142b.

Figure 4C:
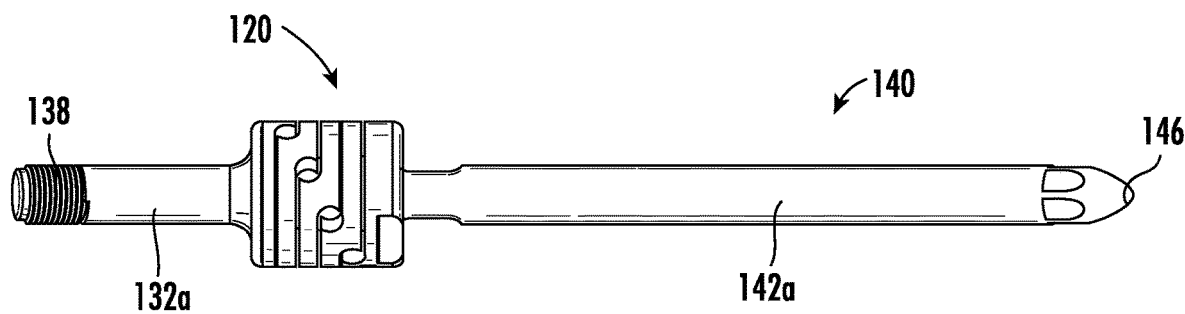
Figure 4D:
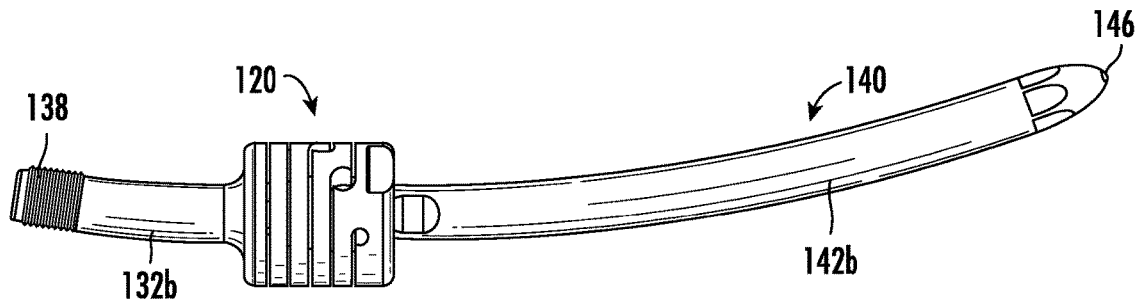

FIG. 4C shows a system configuration, or construct, comprising a flexible coupler 120 with a straight stem 132a attached to a rigid rod 140 with a straight shaft 142a, while FIG. 4D shows a system configuration, or construct, comprising a flexible coupler 120 with a curved stem 132b attached to a rigid rod 140 having a curved shaft 142b.

Figure 4E:
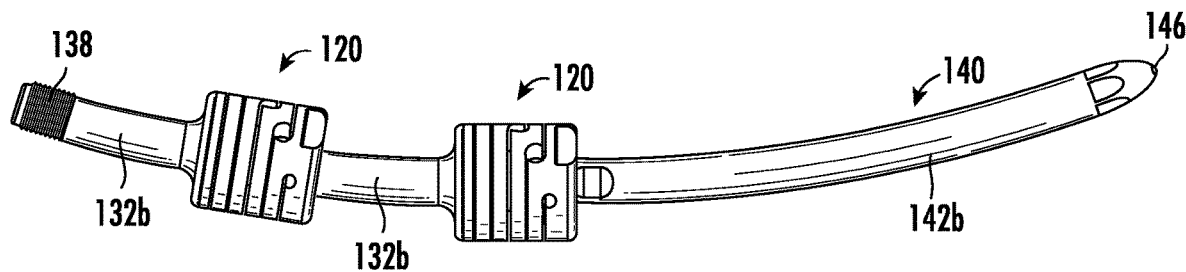
Figure 4F:
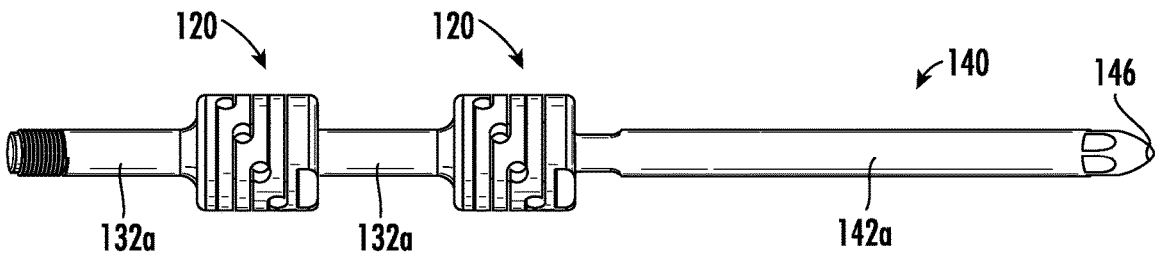

FIG. 4E shows a system configuration, or construct, comprising two flexible couplers 120 and a rigid rod 140, all of which have curved stems 132b or a curved shaft 142b, attached in series together. FIG. 4F shows a system configuration, or construct, comprising two flexible couplers 120 and a rigid rod 140, all of which have straight stems 132a or a straight shaft 142a, attached in series together. Of course, it is understood that any one of those dynamic or rigid components could be substituted with one having a straight stem or shaft as well. The various combinations and configurations or constructs shown are merely for illustration purposes only.

A set of instruments 200 may be provided for implanting the modular spine stabilization system 100. The instruments may be particularly useful for a minimally invasive surgery (MIS) technique.

Figure 5:
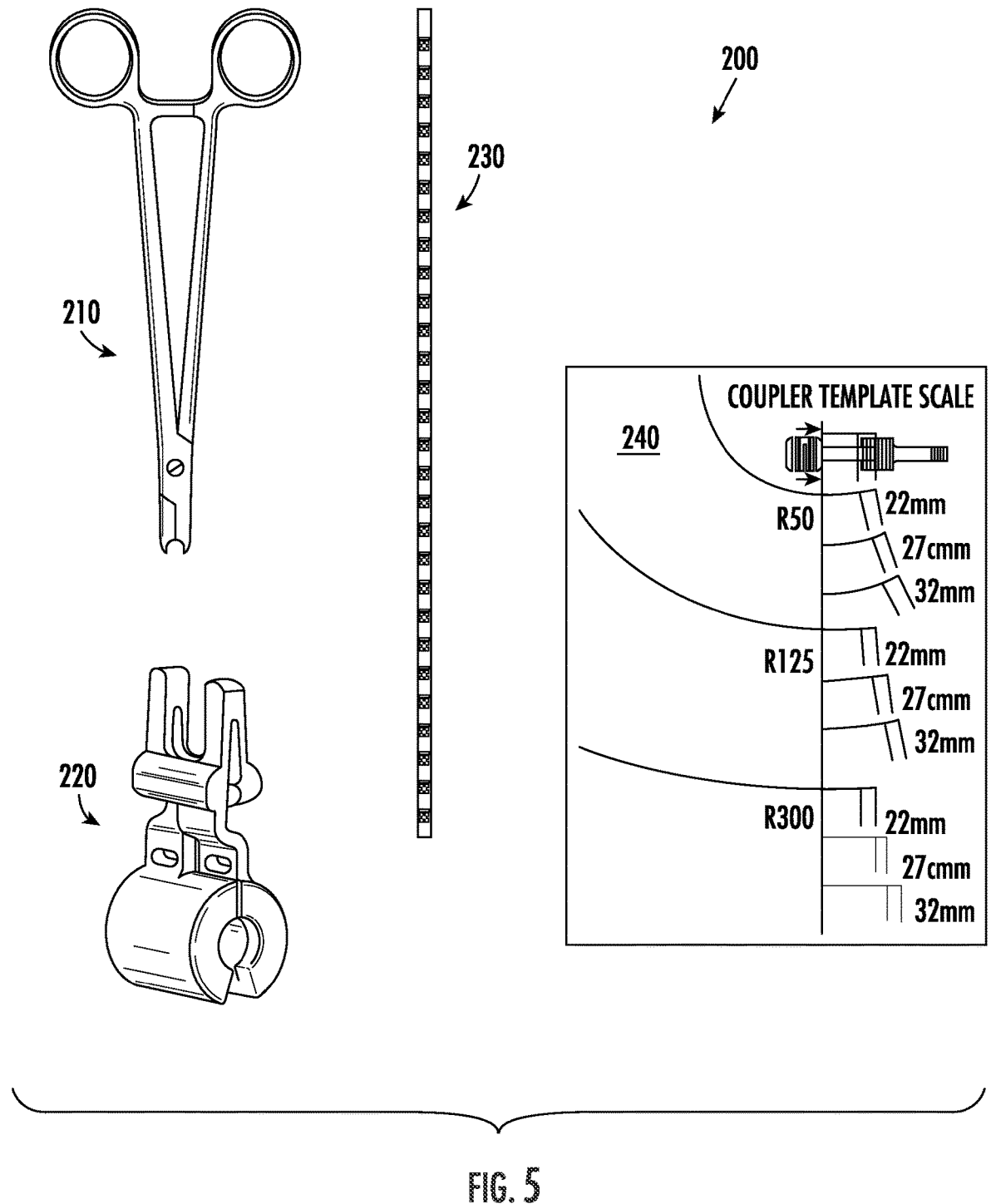
FIG. 5 shows exemplary embodiments of instruments of an instrument set of the present disclosure which are useful for contouring a stem of a flexible coupler.
Figure 6:
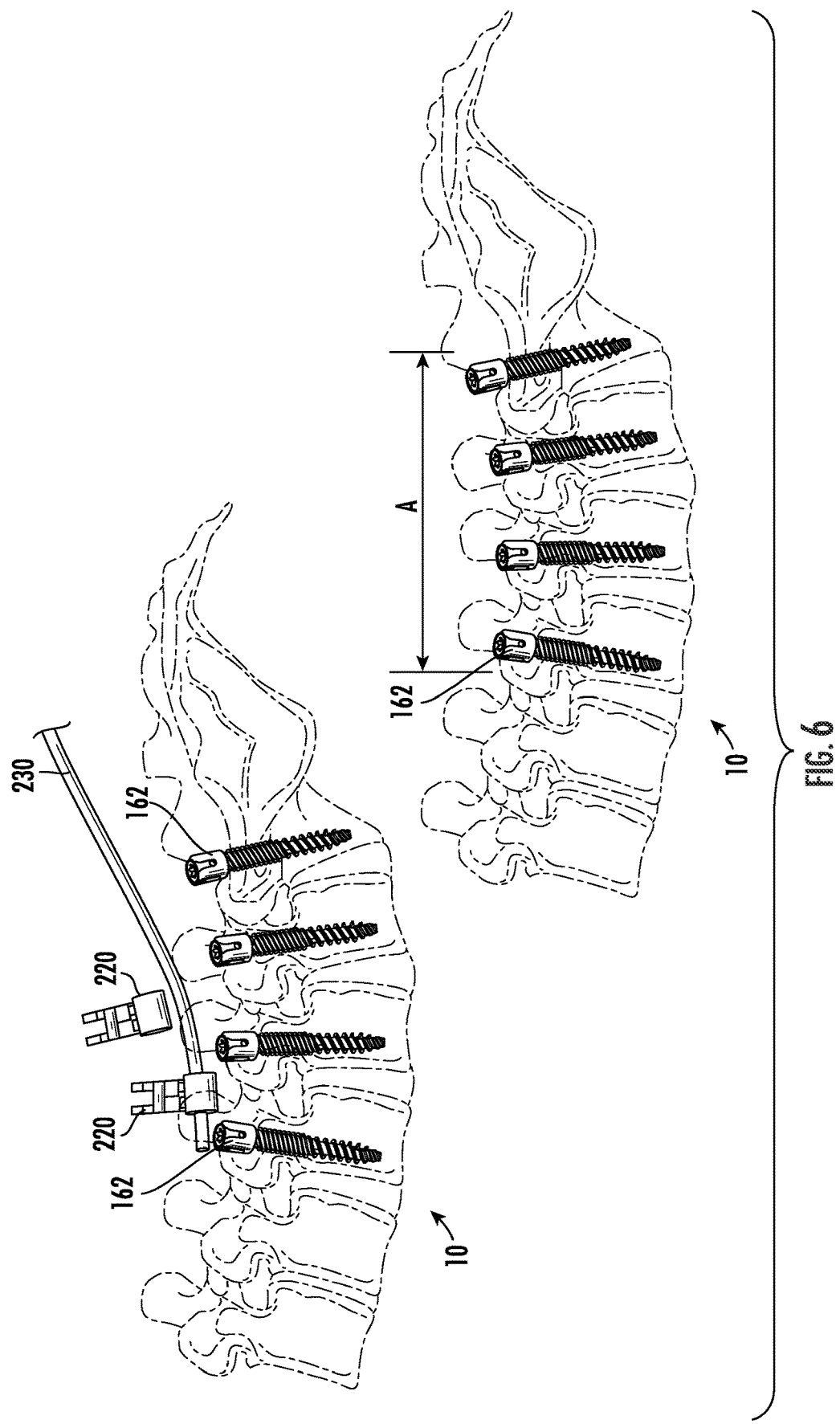
FIG. 6 shows an exemplary method of using some of the instruments of FIG. 5 for determining a curvature of a flexible coupler.

FIG. 5 shows various instruments forming part of the instrument set 200 of the present disclosure that can be used to contour (i.e., bend) the stem 132 of the flexible coupler 120 in order to adapt it to the unique curvature of the patient's spine, as shown in FIG. 6. The patient's spine 10 has a natural curvature that poses a challenge when connecting components such as the flexible couplers 120 of the present disclosure together in series, in order to span and treat multiple levels. By creating a curved stem 132b, the flexible couplers 120 are able to connect end-to-end and mimic the curvature of that portion A of the patient's spine 10 to be treated, and where the flexible couplers 120 are to be implanted. These instruments include a grasper tool 210 which cooperates with a clamping instrument 220 that can hold onto a guide rod 230. A flexible coupler template 240 may be provided which may help the surgeon to approximate the correct angle of the stem 132 (i.e., length and angle of curved stem) based on the size of the flexible coupler 120. Using these tools, the surgeon may be able to select the appropriately sized coupler and also determine the correct contour for the stem 132 of the flexible coupler 120.

Figure 7B:
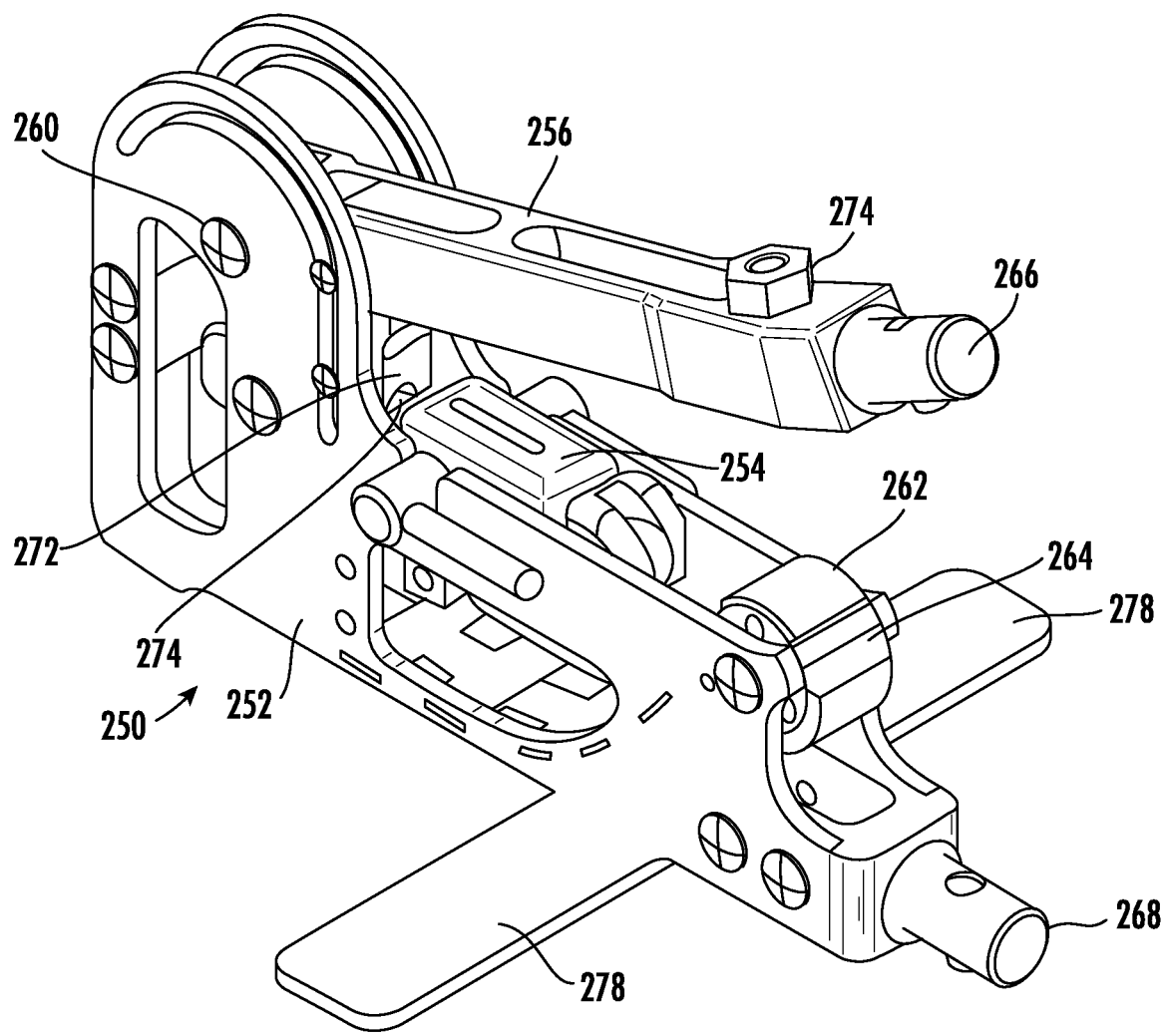
FIG. 7B is a perspective view of the bending instrument of FIG. 7A, without the detachable handles.

Another instrument that forms part of the instrument set 200 of the present disclosure is a bending instrument 250 for bending the stem 132 of the flexible coupler 120. As shown in FIG. 7A, in one exemplary embodiment, the bending instrument 250 may comprise a base or main body 252 configured to attach to detachable handles 270. FIG. 7B illustrates the base 252 without the detachable handles 270, and in greater detail. Within the bending instrument base 252 resides a flexible coupler mounting unit 254. The flexible coupler mounting unit 254 can be pivoted or raised to a perpendicular, 90 degree angle relative to the base 252 after lifting arm 256. This allows the straight stem 132a of the flexible coupler 120 to be inserted into the mounting unit 254, as will be described in greater detail below. The arm 256 attaches to the base 252 with a pivoting hinge mechanism 260. Once the arm 256 is raised, placing the bending instrument 250 in an open position, the flexible coupler mounting unit 254 can be pivoted 90 degrees upward to receive the straight stem 132a of the flexible coupler 120. The arm 256 may include a handle attachment end 266 for attachment to a detachable handle 270. Similarly, the base 254 may also include a handle attachment knob 268 for attachment to a detachable handle 270. Stability bars 278 extending from the base 252 may also be provided, as shown in FIG. 7B.

Figure 8A:
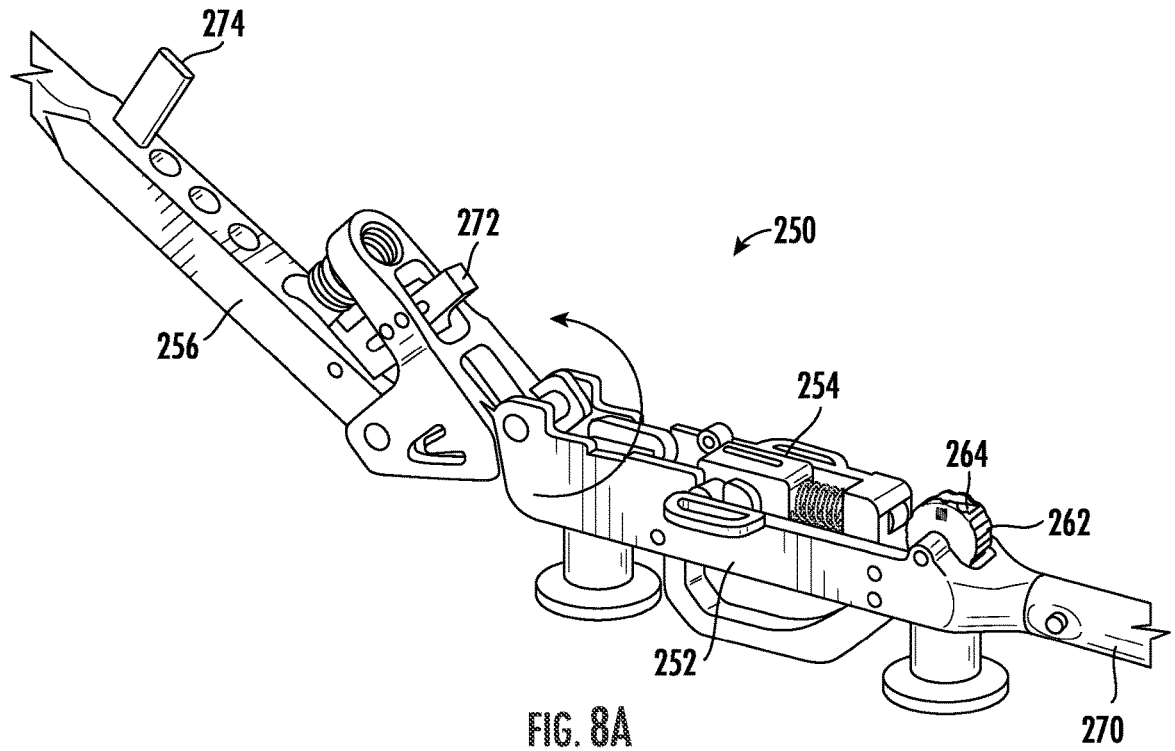
Figure 8B:
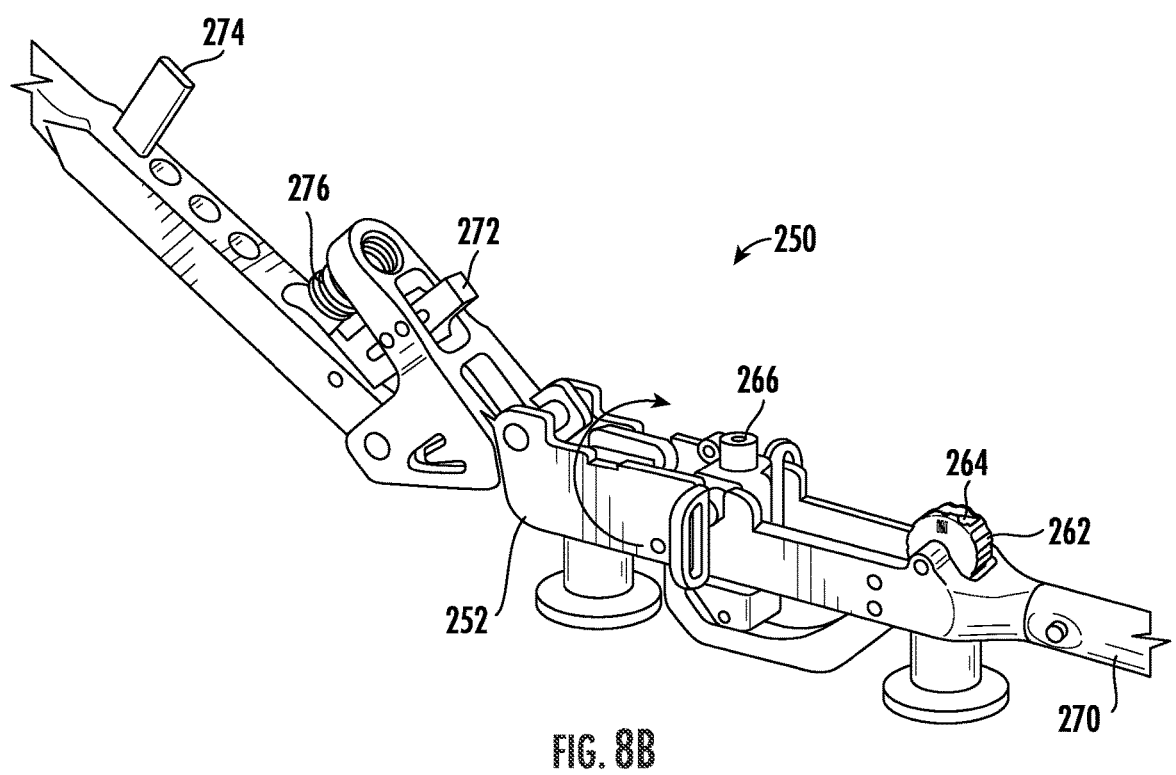
Figure 8C:
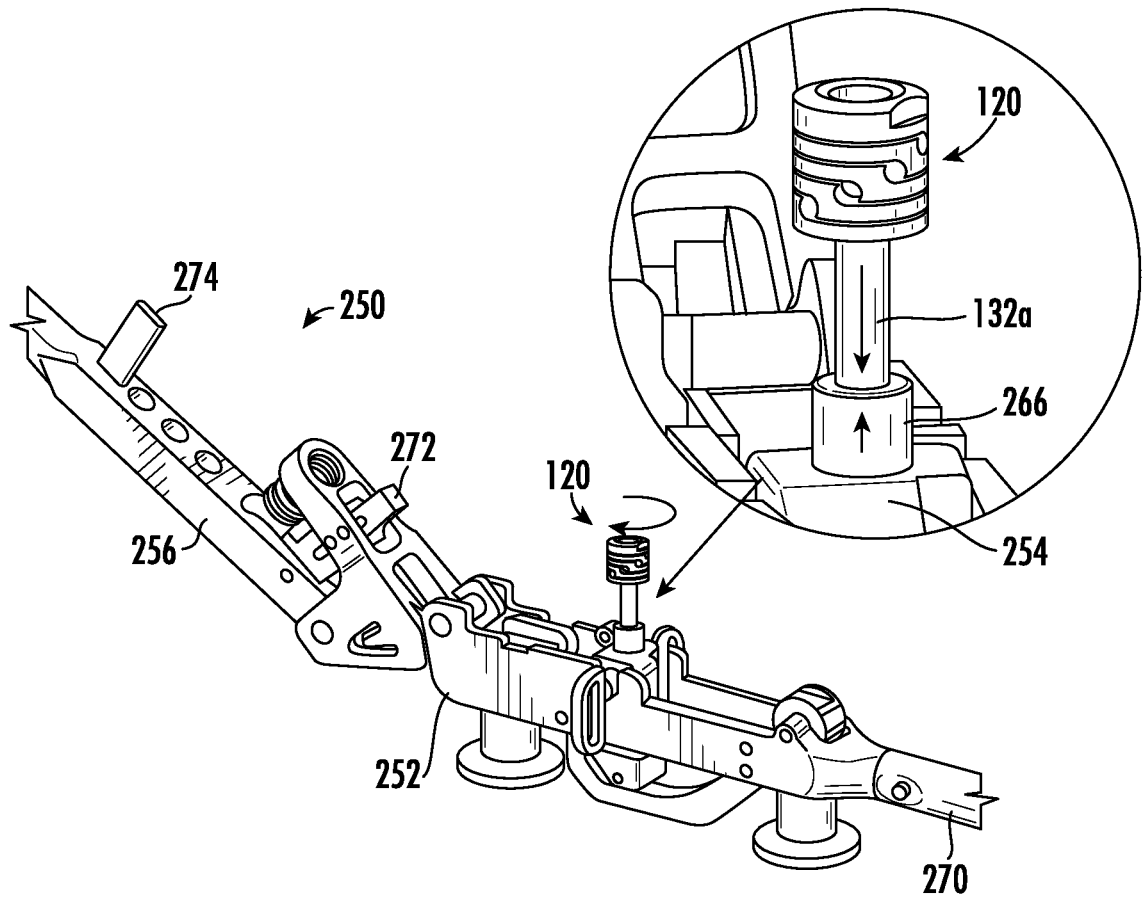

FIGS. 8A to 8H illustrate the steps for bending the straight stem 132a using the bending instrument 250 of FIGS. 7A and 7B. FIG. 8A shows the bending instrument 250 in an open position, i.e., the arm 256 is raised upwards, allowing the flexible coupler mounting unit 254 to swivel or flip upwards 90 degrees on the bending instrument base 252, as shown in FIG. 8B. This pivoting of the flexible coupler mounting unit 254 exposes a portal 266 for receiving the straight stem 132a of the flexible coupler 120. Once the portal 266 is exposed, the selected flexible coupler 120 may be inserted by threading the threaded end 138 of the straight stem 132a into the portal 266 of the flexible coupler mounting unit 254 of the bending instrument 250, as shown in FIG. 8C.

Figure 8D:
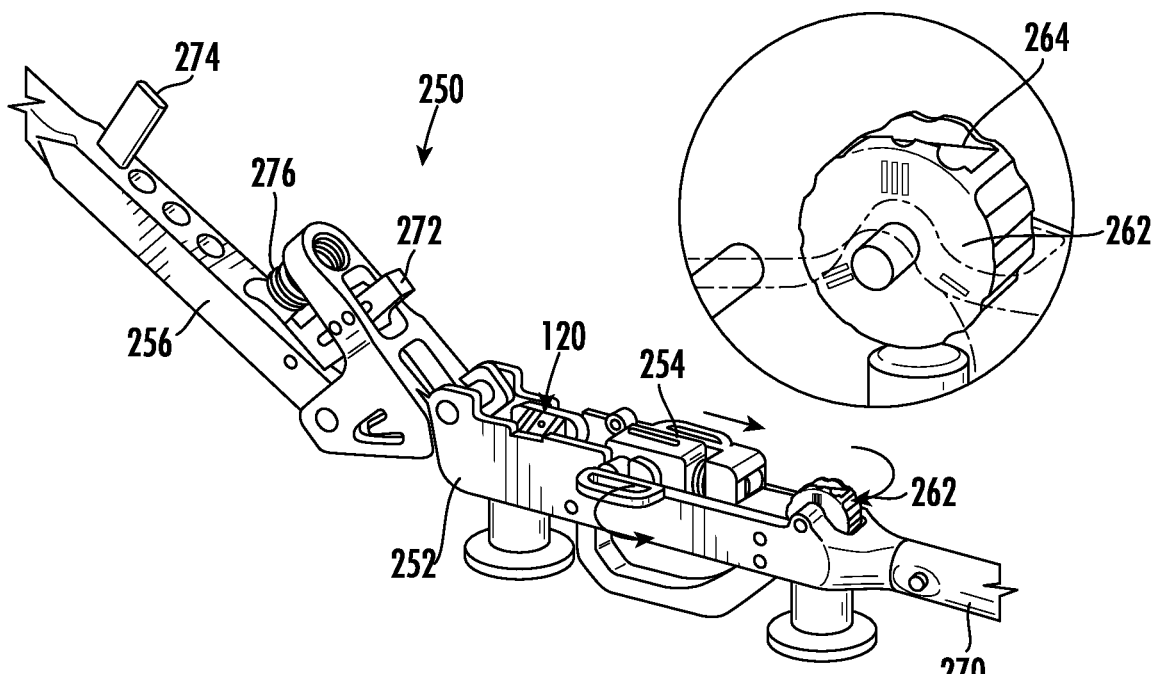

Next, the desired radius of curvature for the straight stem 132a is selected by dialing the appropriate degree of bending on the radius selection wheel 262. As previously discussed, the desired radius of curvature may be selected using the template 240 provided as a selection guide. This radius selection wheel 262 includes various angled ramps or detents 264 about its circumference. Rotation of the radius selection wheel 262 exposes a particular angled ramp or detent 264, as represented in FIG. 8D, in which the flexible coupler mounting unit 254 is pivoted back 90 degrees counterclockwise to lay within the base 252.

Figure 8E:
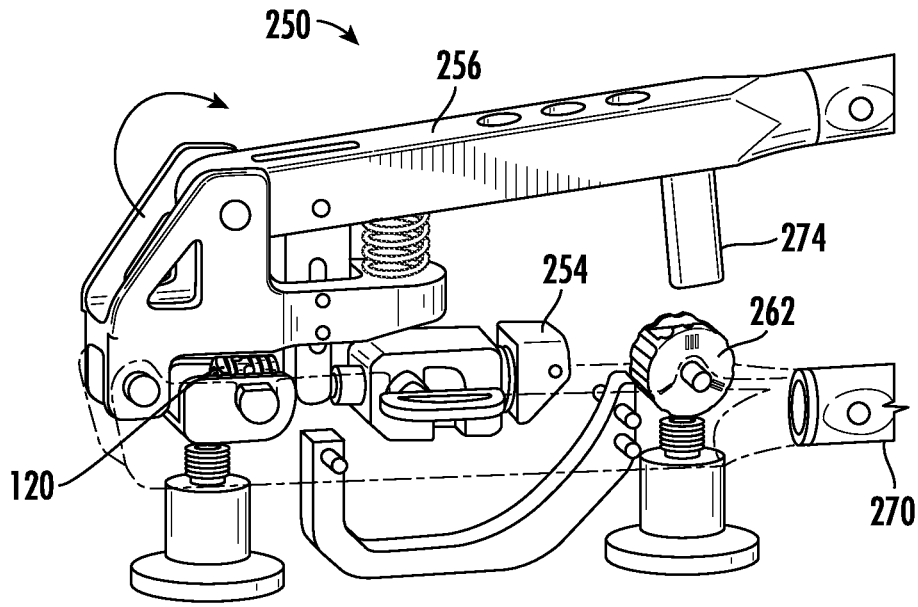
Figure 8F:
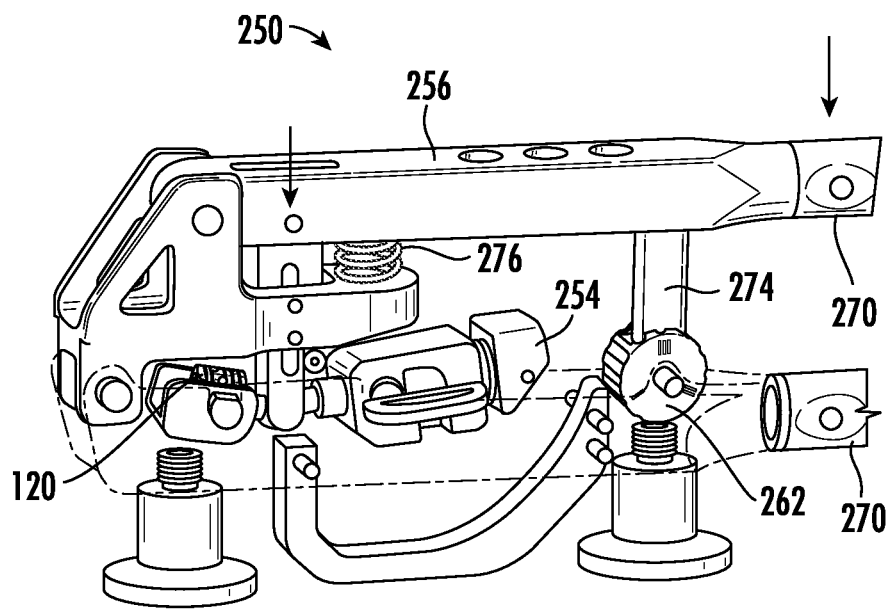

After the correct radius has been chosen and the radius selection wheel 262 rotated to the correct position corresponding to the chosen radius, the arm 256 of the bending instrument 250 may then be lowered, as shown in FIG. 8E. In the process of lowering the arm 256, a protruding pusher bar 274 extending from the arm 256 pushes against the radius selection wheel 262 at the selected detent 264, as shown in FIGS. 8E and 8F. A pusher head 272 extending from the arm 256 urges against the straight stem 132a with a corresponding amount of force, thus bending the straight stem 132a of the flexible coupler 120. The pusher head 272 may have at a free end a contoured or curved contact surface 274 to allow it to effectively push against the cylindrical outer surface of the stem 132a when in contact.

Figure 8G:
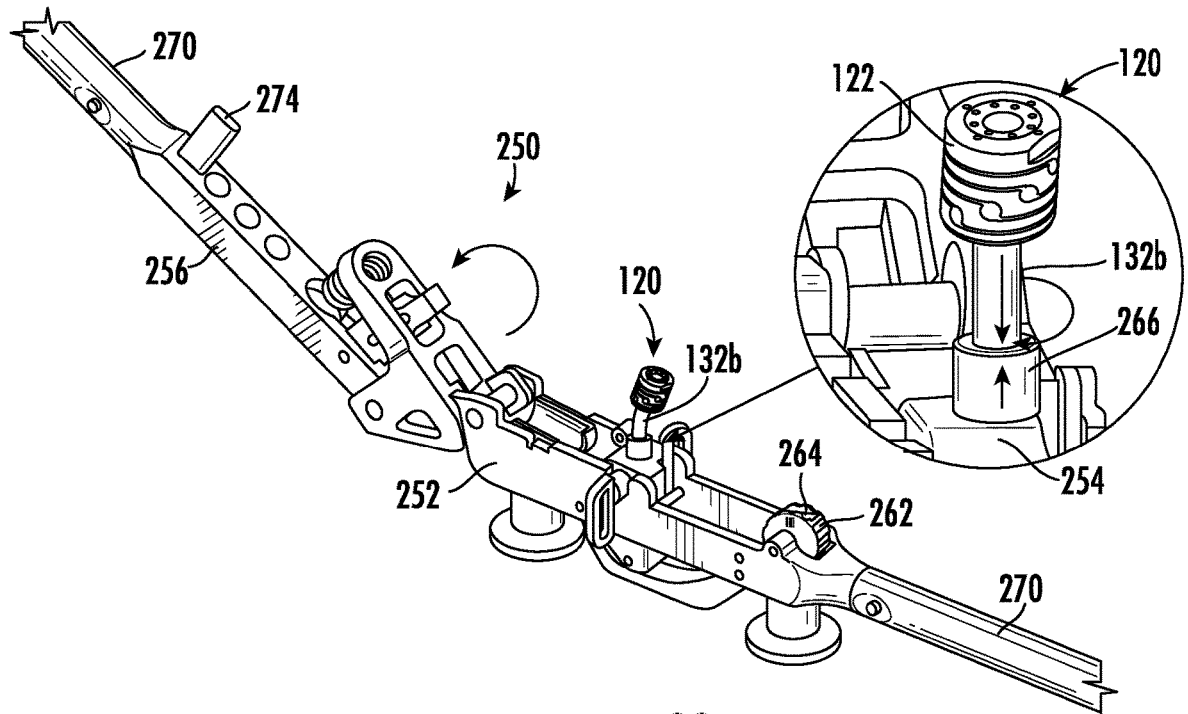
Figure 8H:
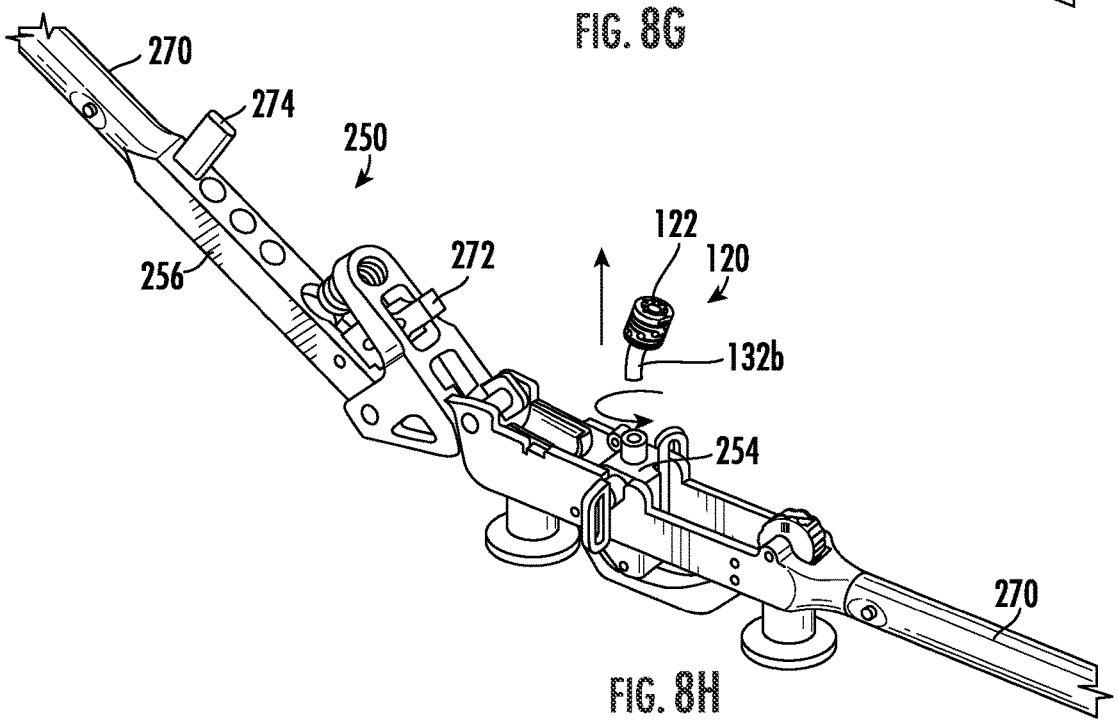

In some embodiments, a damper in the form of a spring 276 may be provided, as shown, to facilitate the lowering of the arm 256 against the bending instrument base 252. Likewise, the detachable handles 270 which are attached to the bending instrument base 252 at attachment knob 268 as well as the arm 256 at attachment end 266 also help facilitate the lowering of the arm 256 against the base 252 to place the instrument 250 in a fully closed position. Once the bending instrument 250 is in its fully closed position with the flexible coupler 120 within the flexible coupler mounting unit 254, the stem 132 is bent to the desired radius chosen. FIG. 8G shows the bending instrument in the open position with the arm 256 raised to allow the flexible coupler mounting unit to swivel upwards. The flexible coupler 120 with the now bent stem 132b can be removed from the portal 266 by unscrewing it from the flexible coupler mounting unit 254, as shown in FIG. 8G. FIG. 8H shows the flexible coupler fully removed from the bending instrument 250.

Figure 9A:
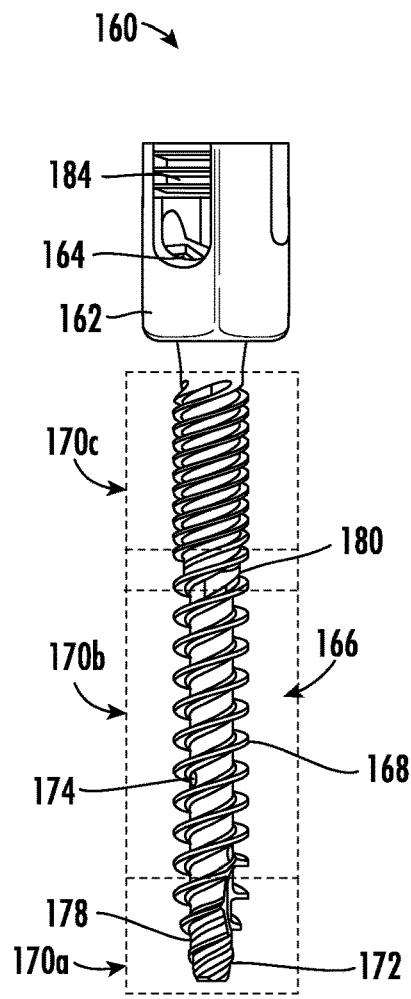
FIG. 9A is a front view of an exemplary embodiment of a bone fastener of the present disclosure for use with the modular spine stabilization system.
Figure 9B:
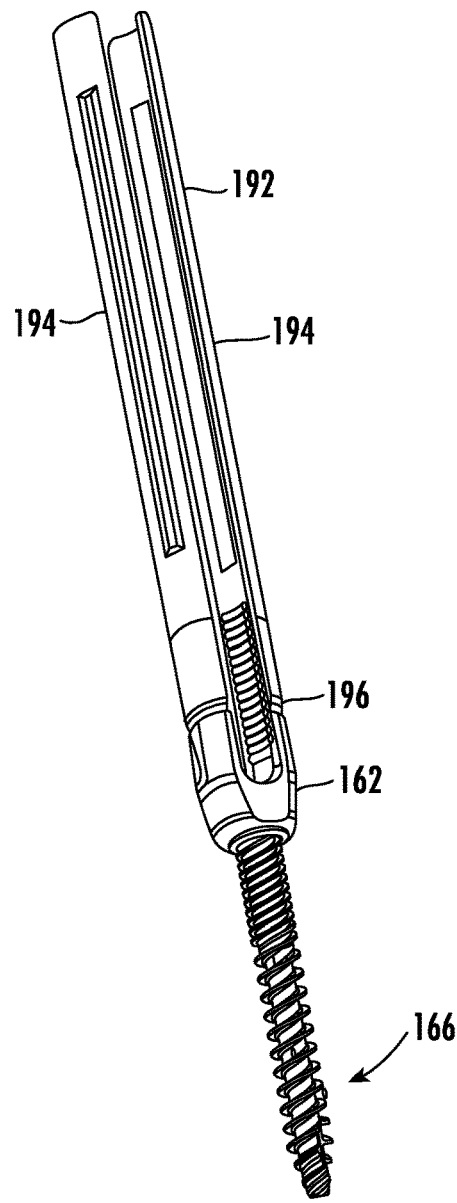
FIG. 9B illustrates a perspective view of the bone fastener of FIG. 9A and having an attached extended head portion.

FIG. 9A illustrates one exemplary embodiment of a bone fastener 160 for use with the modular spine stabilization system 100 of the present disclosure. The bone fastener 160 may comprise a head portion 162 shaped like a tulip and a shank portion 166. The head portion 162 may include a cavity 164 for receiving an implantable device, and an enlarged head 184 of the shank portion 166 which may sit within the cavity 164. The diameter of the head portion 162 may be in the range of about 5.5 to 9.5 mm. The shank portion 166 may include an elongated shaft 168 extending from the enlarged head 184 to a distal tip 172. The enlarged head 184 may include a tool-engaging opening 186, as shown in FIG. 9D.

The shaft 168 of the shank portion 166 may be defined by a first leading threaded portion 170a adjacent the distal tip 172, a second trailing threaded portion 170c adjacent the head portion 162, and an intermediate threaded portion 170b extending between the first and second threaded portions.

According to one aspect of the present disclosure, the first leading threaded portion 170a can include quad lead threads, and the second trailing threaded portion 170c can include quad lead threads. Further, the shaft 168 may have the same nominal diameter (i.e., outer thread diameter) throughout the entire length of the shaft.

According to another aspect of the present disclosure, the shank portion 166 has a generally uniform diameter from the second trailing threaded portion 170c to the end of the intermediate threaded portion 170b. The pitch of the intermediate threaded portion 170b may be between about 4 and 5 mm. A conical part 180 may be provided in the transition between the second trailing threaded portion 170c and the intermediate threaded portion 170b, while the second trailing threaded portion 170c is generally cylindrical. The intermediate threaded portion 170b may include dual lead threads, in one embodiment.

The first leading threaded portion 170a may have a conical shape in some embodiments. In some embodiments, the first leading threaded portion 170a may include cutting notches 178, as shown in FIG. 9A. The bone fastener 160 may be provided with cement holes 174 in some embodiments, as shown. Additionally, the bone fastener 160 may be color coded for different sizes, and may be configured with a self-tapping distal tip 172.

As shown, a locking device 184 for securing the implantable device within the cavity 164 may be provided. This locking device 184 may be a set screw, for example. The head portion 162 may be an extended tulip head, to accommodate minimally invasive surgery (MIS) instrumentation and techniques during implantation. FIG. 9B shows a perspective view of the extended tulip head 192, which also includes extended walls 194 forming the tulip head extension and being attached at a scored or cutaway portion 196 that can be broken off from the tulip head 162 after use.

Figure 9C:
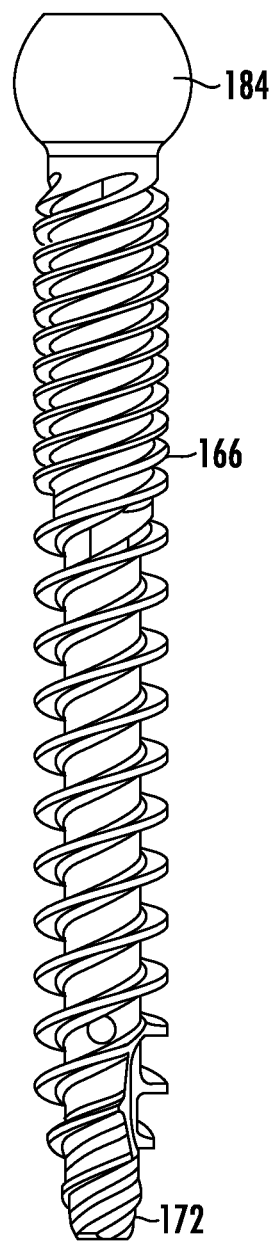
FIG. 9C illustrates a shaft for use with the head portion of the bone fastener of FIG. 9A.
Figure 9D:
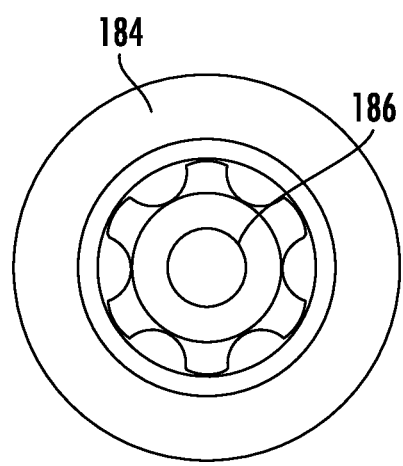
FIG. 9D illustrates a top-down view of the shaft of FIG. 9C, in which the head region may include an extended tulip head.

FIG. 9C illustrates a detailed view of the shaft 166, while FIG. 9D illustrates a top-down view of the shaft 168, both without the attached tulip head portion 162.

Although the exemplary embodiment described and shown has a first leading threaded portion 170a with quad lead threads, and a second trailing threaded portion 170c with quad lead threads, it is contemplated that other types of lead threads can also be utilized such as dual lead threads, if so desired. For example, any of the threaded portions 170a, 170b, 170c of the shank 166 may be provided with double, triple or quad lead threads, although quad lead threads will provide enhanced bone purchase.

Figure 10A:
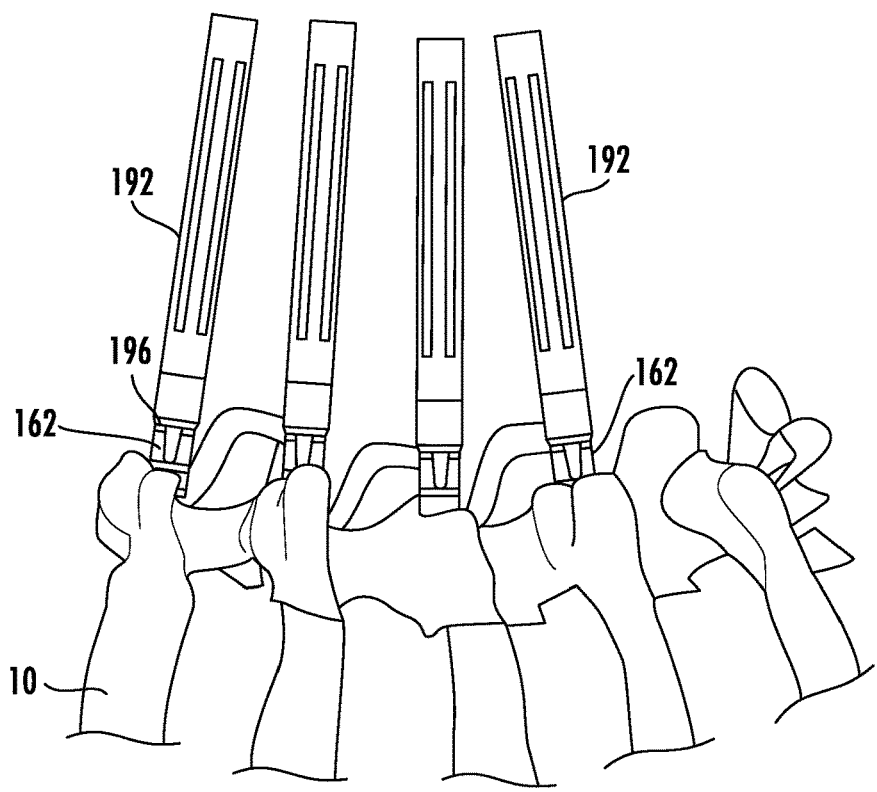
FIGS. 10A and 10B illustrate a method of using the bone fastener of FIGS. 9A to 9D to secure the modular spine stabilization system of FIG. 1.
Figure 10B:
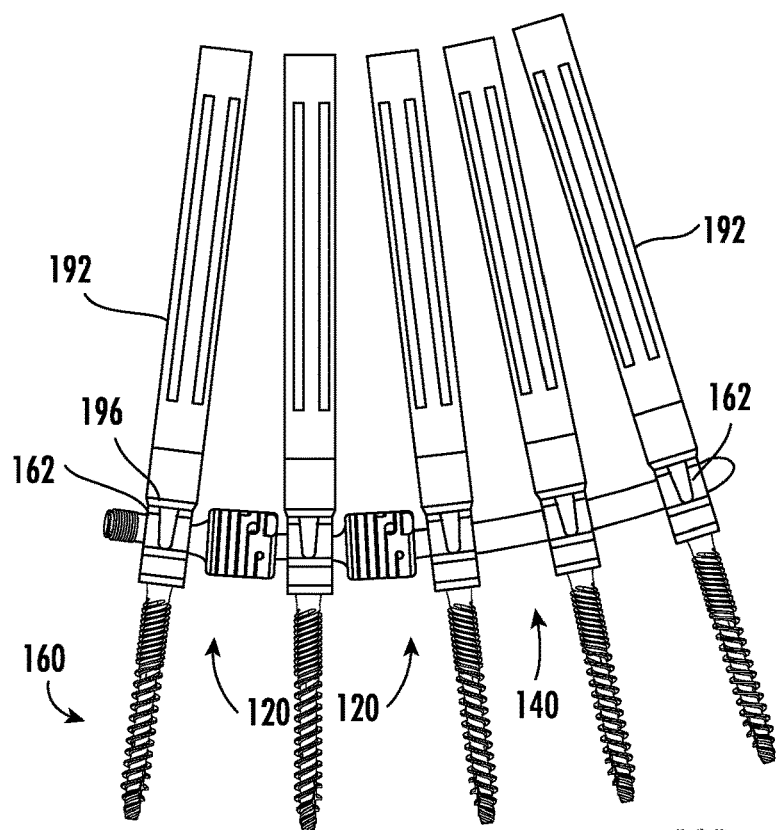

FIGS. 10A and 10B illustrate an exemplary method of using the bone fasteners 160 having the tulip head extension 192 attached thereto with the modular spine stabilization system of the present disclosure. FIG. 10A shows the bone fasteners 160 with attached tulip head extensions 192 inserted into the patient's spine, while FIG. 10B shows the system configuration or construct now placed within the bone fasteners 160. These tulip head extensions 192 are particularly helpful for MIS techniques. In addition, the tulip head extensions 192 can be useful for performing rod reduction procedures. Once the assembly of the stabilization system is completed, and the subcomponents flexible couplers and rigid rods are in their desired arrangement and secured with the bone fasteners 160, the tulip head extensions 192 may be broken off at the scored regions 196.

While the assembly of the present system is described as a MIS technique, it is of course understood that the spine stabilization system can be assembled with tradition open surgical techniques as well. To facilitate this assembly in open surgery, bone fasteners 160 may be provided having tulip head extensions but of a shorter relative length than for those to be used in a MIS technique.

Turning back to the instrument set 200, it is contemplated that instruments such as a trocar awl, awl, screw dilator, dilator, and screw length ruler may be provided. In addition, a tap, for instance, with a ¼ inch coupling, a tap with a dilator and T-handle with a ratchet, a polyaxial screwdriver, for example, having a straight handle and a T-handle alternative, and a nut driver, for instance, with a ¼ inch coupling, may also be provided within this instrument set 200 as well.

In addition, FIGS. 11A to 11C show various views of an exemplary embodiment of a flexible coupler and rod inserter tool 280 that may be part of the instrument set 200 of the present disclosure. The inserter tool 280 may include an arm 282 extending into a gripping end 284 for holding onto a flexible coupler and rigid rod construct, a handle 286, and have a pivotable neck 288 connecting the arm 282 and handle 286, as shown in FIG. 11A, which would allow the angular insertion of the implantable components of the modular spine stabilization system 100. The pivotable neck 288 is angularly adjustable, and may be locked in position using a tightening nut 312, for example, as shown in FIG. 11A in the enlarged view. This inserter tool 280 may be especially helpful when inserting by a MIS technique. The gripping end 284 may include curved walls 292 that are configured to firmly grasp the flexible coupler body 122, while finger projections 294 may be provided to support and stabilize the elongated shaft 142 of the rigid rod 140 extending from the flexible coupler and rigid rod construct, as shown in FIG. 11B. These finger projections 294 may be operatively movable from an open position (FIG. 11B) into a closed position for firmly gripping the flexible coupler body 122, as shown in FIG. 11C.

Figure 12A:
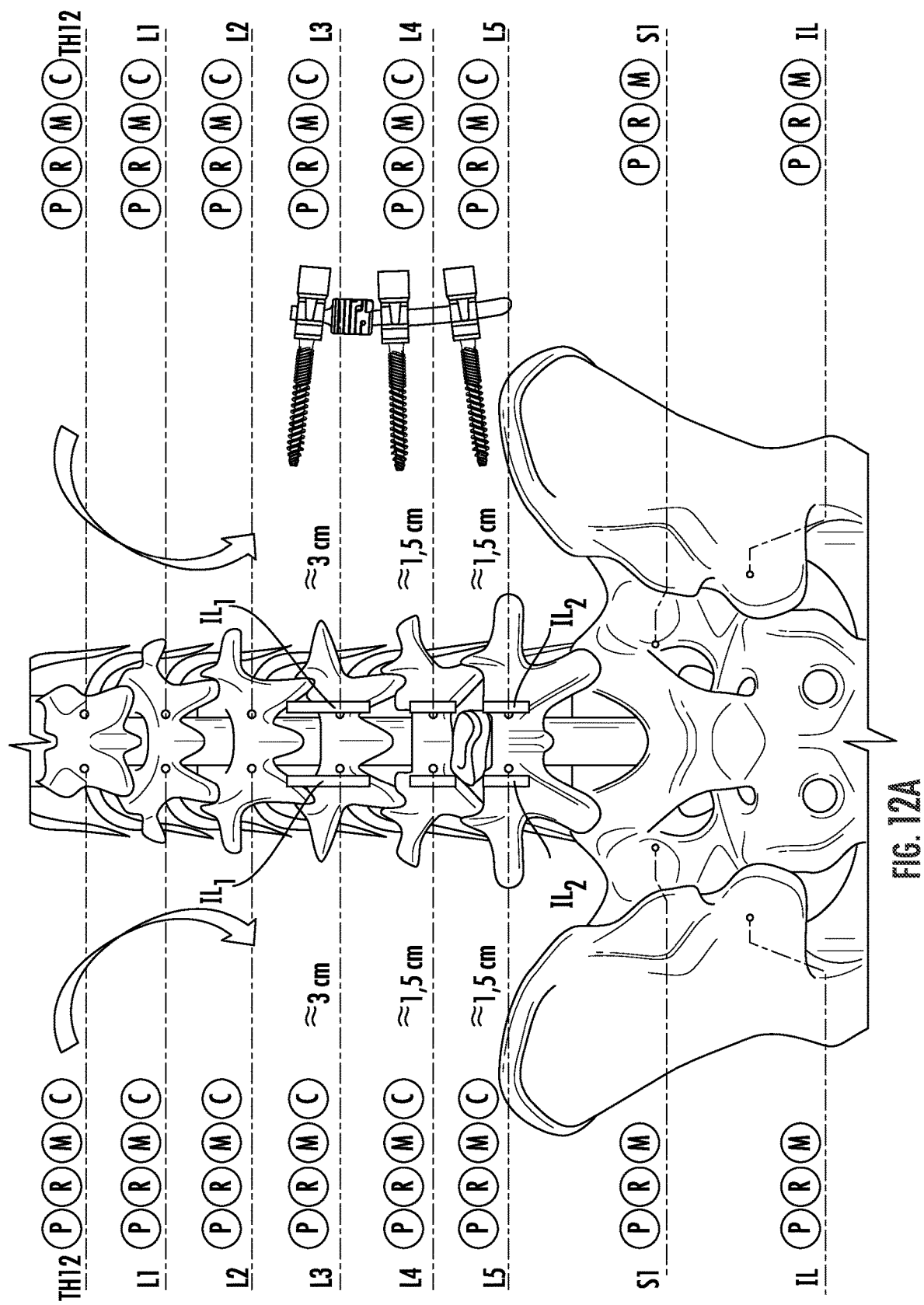

In the illustrated embodiment, the flexible coupler 120 is threadedly connected to a rigid rod 140, and the construct is grasped by the flexible coupler and rigid rod inserter tool 280. As shown in FIG. 12A, incisions can be made to enable the inserter tool 280 to access the spine 10. The upper-most incision lines $IL_1$ indicate the suggested length and location for the incisions for enabling access of the inserter tool 280. The incisions may be, for example, about 3 cm in length. The second set of shorter incision lines $IL_2$ (e.g., 1.5 cm) as shown below upper-most incision lines $IL_1$ are for the insertion of the bone fasteners 160 at the adjacent levels.

Figure 12B:
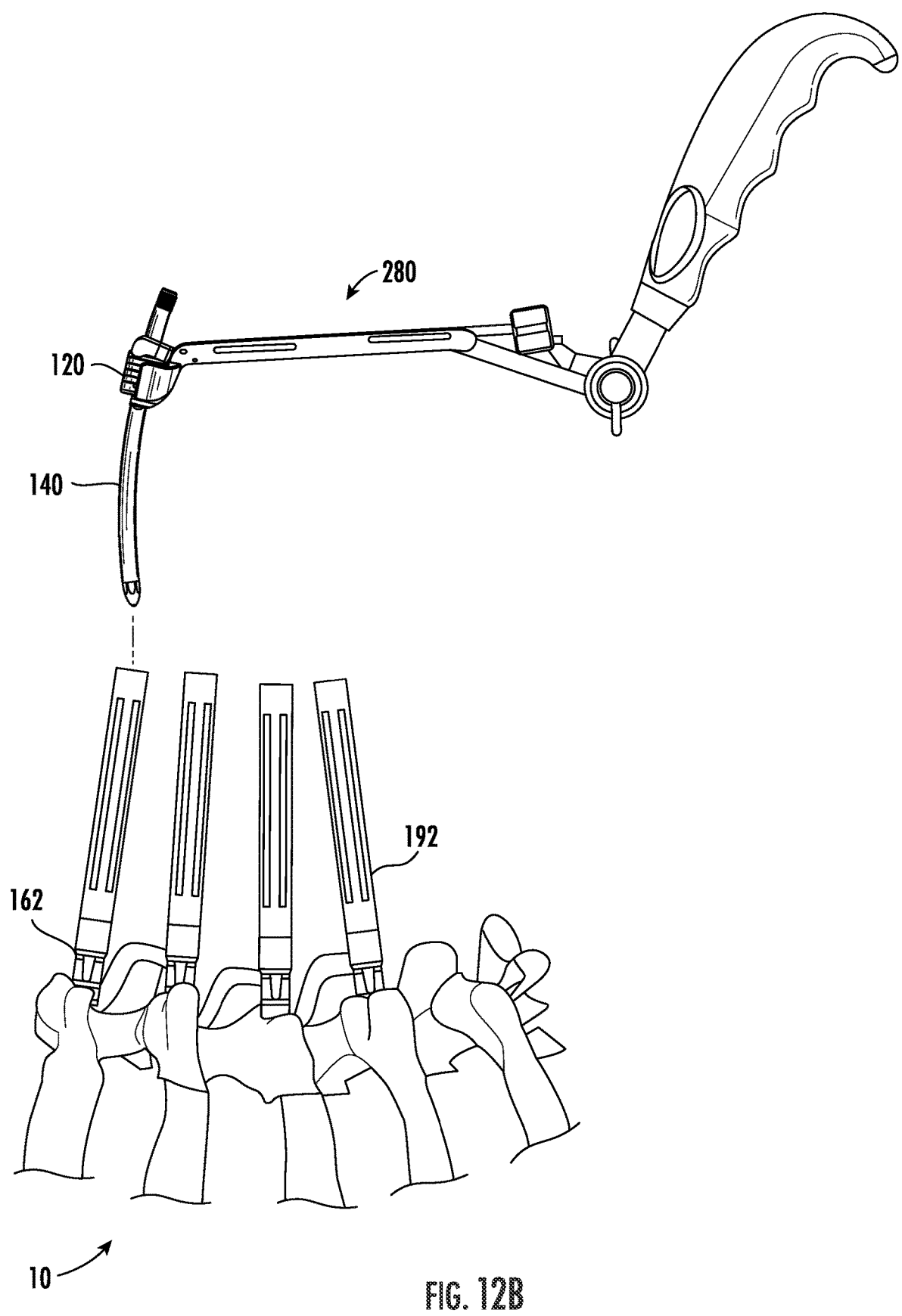
Figure 12C:
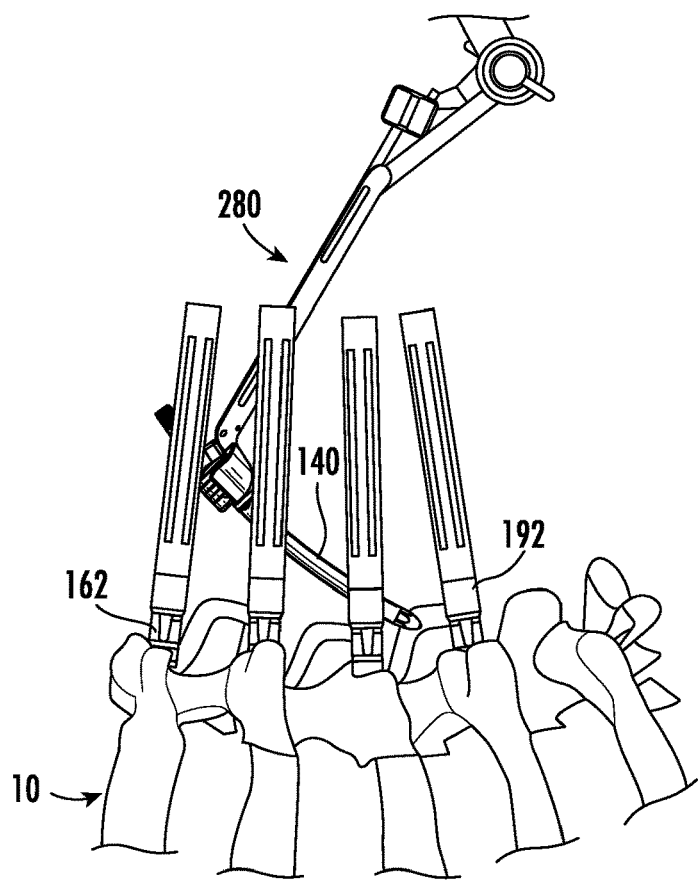
Figure 12D:
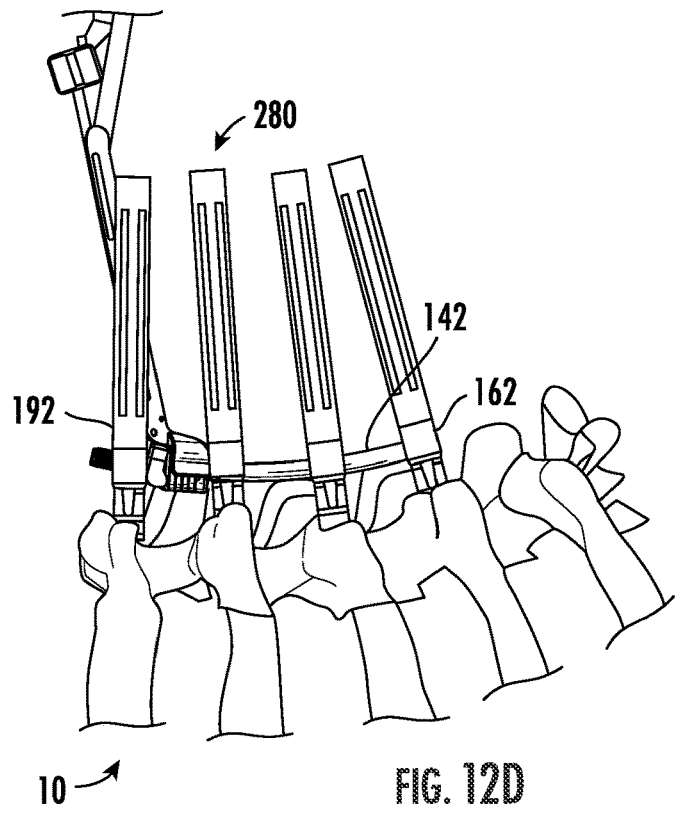
Figure 12E:
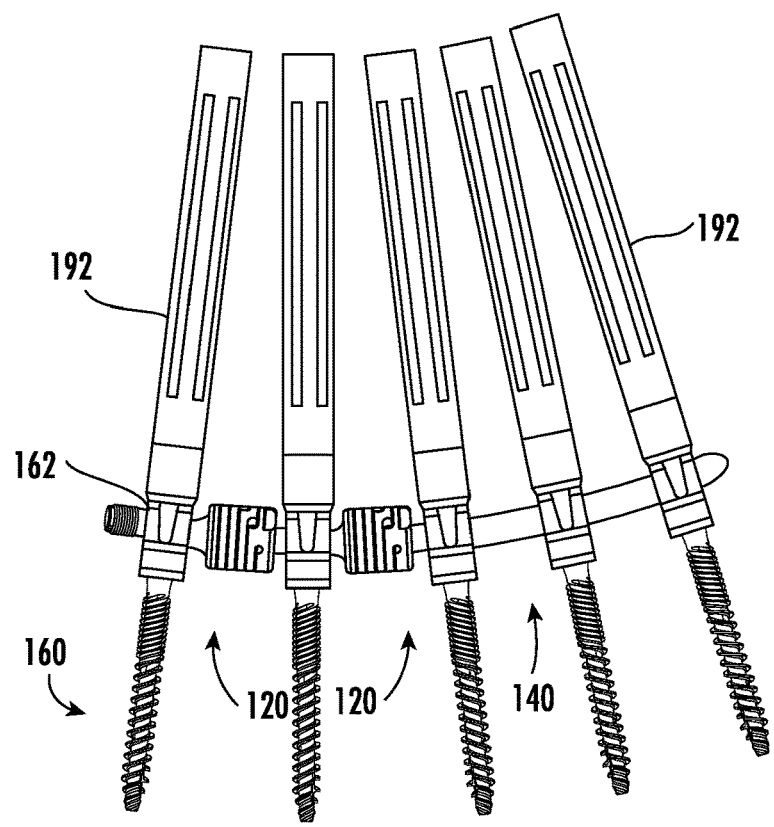

FIGS. 12B to 12D illustrate a method of using the inserter tool 280 to introduce the flexible coupler and rigid rod construct into the patient, whereby the inserter tool 280 is able to hold the flexible coupler and rigid rod construct while positioning it between the walls 294 of the extended tulip extensions 292, and seat the construct into the heads 162 of the bone screws 160. The angled and adjustable neck 288 of the inserter tool 280 enables the user to have the necessary angle of approach to perform the steps in a minimally invasive manner.

Figure 13:
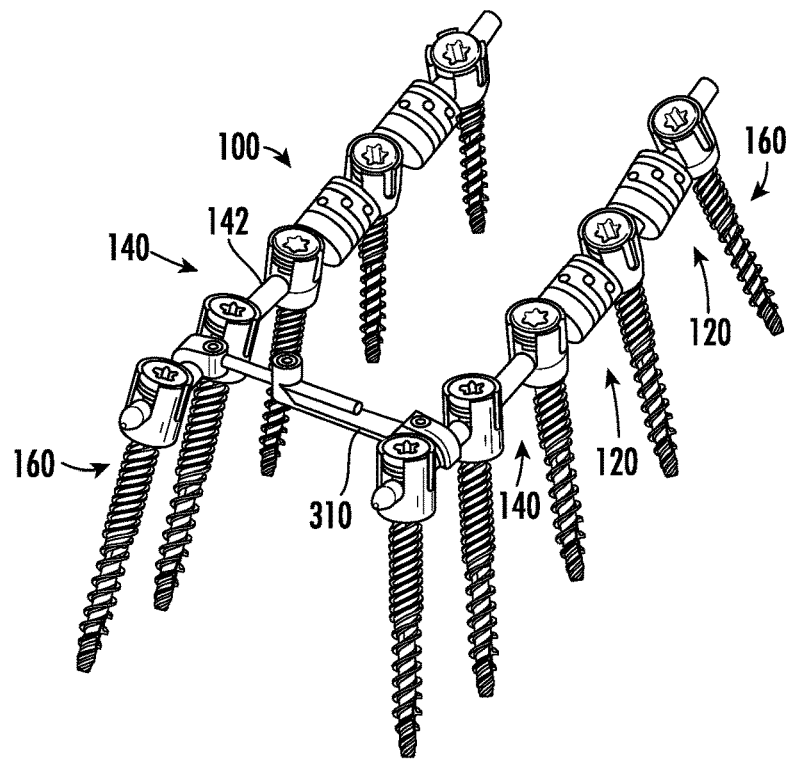
FIG. 13 is a perspective view of the modular spine stabilization system of the present disclosure in use with a crosslink.

The modular spine stabilization system 100 of the present disclosure may be used for stabilization of both sides of a patient's spine, as illustrated in FIG. 13 in which a series of flexible coupler to rigid rod constructs may be assembled for implantation along both sides of the spine. In such a case, a crosslink 300 may be used to further stabilize the system 100. Accordingly, a measurement tool may be provided with the instrument set 200 to determine the appropriate length of the crosslink 310 to use.

Figure 14A:
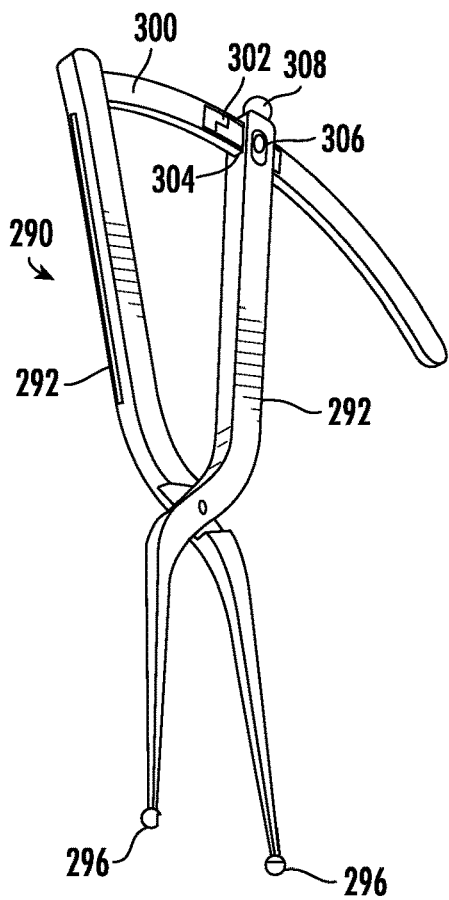
FIG. 14A is a perspective view of an exemplary embodiment of a measurement tool of the instrument set of the present disclosure, for determining a crosslink length.

An exemplary embodiment of a measurement tool 290 is shown in FIG. 14A. The measurement tool 290 may include a pair of pivoting arms 292 hinged together in a manner similar to scissors or pliers, with one end of the pivoting arms 292 interconnected and cooperating to indicate measurement size. As shown, one of the pivoting arms 292 may include a laterally extending bar 300 having indicia 302 representing units of length thereon, while the other pivoting arm 292 may have a slot 304 for slidingly receiving the laterally extending bar 300. This same pivoting arm 292 may further include a window 306 through which the user may view the indicia 302 on the laterally extending bar 300 as it slides across the slot 304. A locking nut 308 may be provided to lock the laterally extending bar 300 within the slot 304 and prevent further movement of the pivoting arms 292.

Figure 14B:
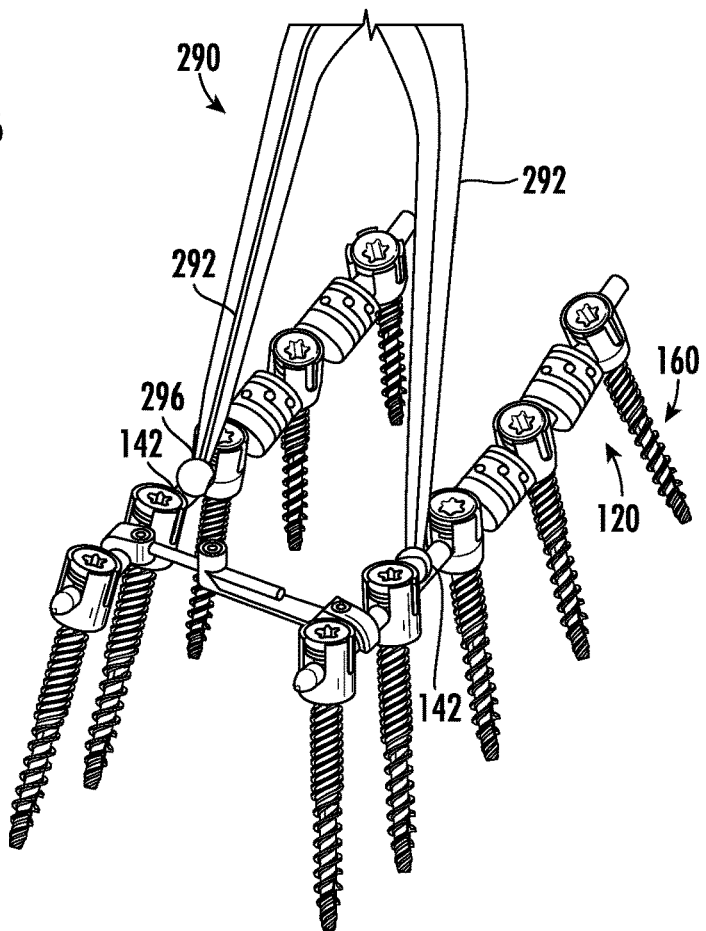
FIG. 14B shows the measurement tool of FIG. 14A in use to measure a distance between two pairs of rods.

At the opposite end of the pivoting arms 292 are tips 296 configured to be placed on the elongated shafts 142 of laterally opposed rigid rods 140 for measuring the distance between the rigid rods 140 located on opposed sides of the spine, as shown in FIG. 14B. For instance, as shown in FIG. 14A, the tips 296 may have a curved inner surface for placement against the cylindrical surface of the elongate shafts 142, similar to the manner shown in FIG. 14B. This measured distance can then determine what length crosslink 310 would be suited for use at this level.

Figure 15A:
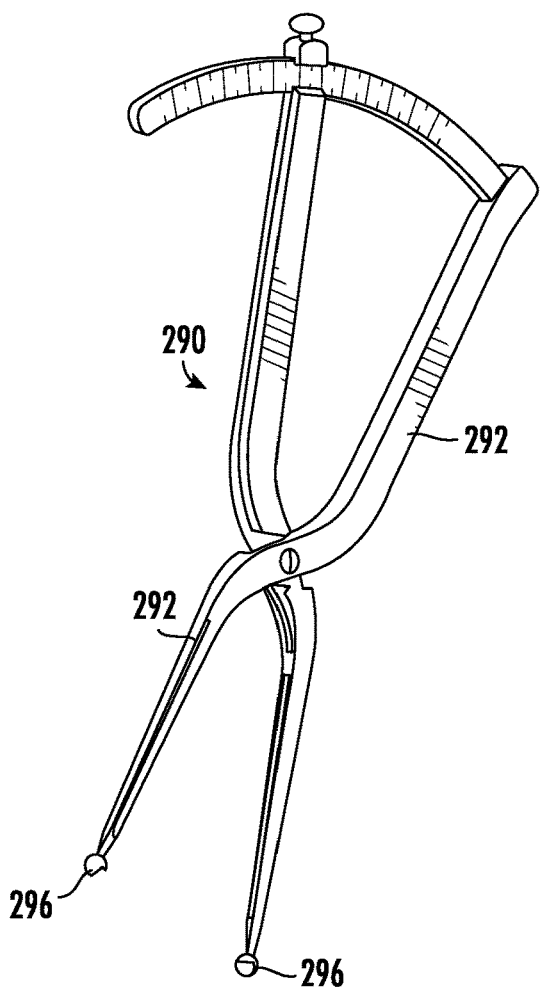
FIG. 15A is a perspective view of another exemplary embodiment of a measurement tool of the instrument set of the present disclosure, for measuring a length of a system configuration.
Figure 15B:
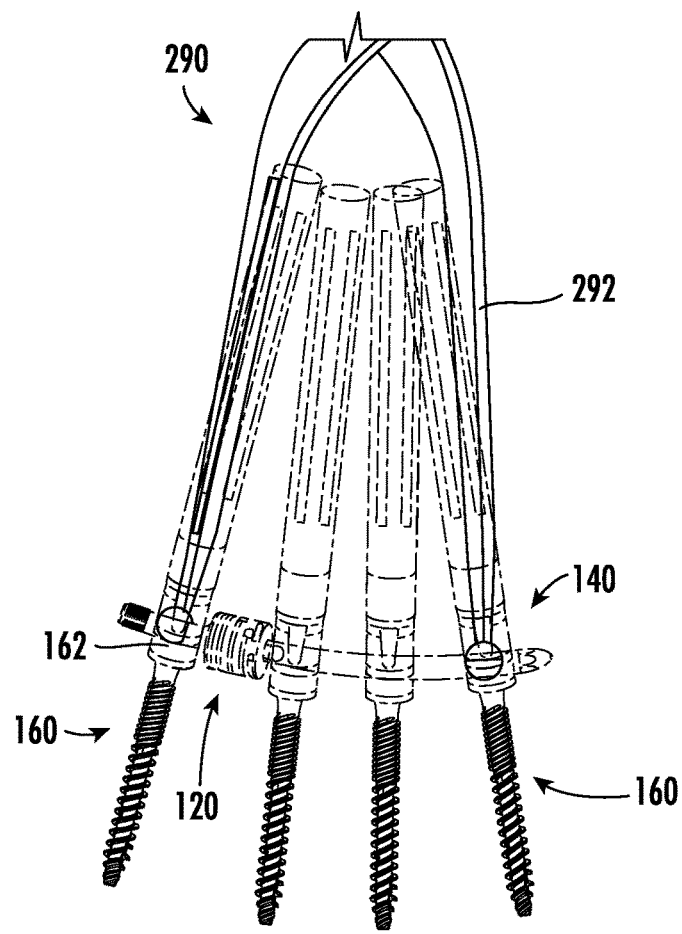
FIG. 15B shows a partial cutaway view of the measurement tool of FIG. 15A in use to measure a length of a system configuration.

In another embodiment, the tips 296 may be configured for placement within the set screws 184 inside the head portions 162 of bone screws 160, in order to measure the length between the bone screws 160, as shown in FIG. 15B. As shown in FIG. 15A, the tips 296 may be shaped and sized to seat within the set screws 184. When used in this manner, the measurement tool 290 can also serve to determine the length of a construct, or between bone screws 160, on the same side of the spine.

While FIG. 13 shows an embodiment in which the pair of constructs is essentially mirror images of one another, it is also understood that there can be variances between one of the constructs of the pair. For example, it is possible that one could use a coupler at one level, on one side, and then a rod at the same level, on the opposite side, of the spine.

Other embodiments will be apparent to those skilled in the art from consideration of the specification and practice of the embodiment disclosed herein. It is intended that the specification and examples be considered as exemplary only, with a true scope and spirit of the embodiment being indicated by the following claims.

What is claimed is:

1. An implantable, modular spine stabilization system, comprising:
    one or more flexible couplers configured to dynamically stabilize a spinal segment of a patient's spine, each flexible coupler having a flexible main body and a bendable stem extending therefrom, each of the one or more flexible couplers having a recess in the flexible main body configured to receive another of the one or more flexible couplers or a rigid rod, wherein the flexible main body is flexible from a proximal end to a distal end thereof;
    one or more rigid rods configured to rigidly stabilize a spinal segment of the patient's spine, each rigid rod having an elongated shaft and configured to be secured in one of the one or more flexible couplers; and
    one or more bone fasteners configured to attach the one or more flexible couplers or rigid rods to the patient's spine, each of the one or more bone fasteners comprising a head portion including a cavity configured to receive one of the one or more flexible couplers or one of the one or more rigid rods, and a shank portion extending from the head portion, the shank portion including an elongated shaft extending to a distal tip, the shank portion having an enlarged head captured within the cavity of the head portion and being defined by a first leading threaded portion adjacent the distal tip, a second trailing threaded portion adjacent the head portion, and an intermediate threaded portion extending between the first and second threaded portions, wherein the first leading threaded portion includes quad lead threads and the second trailing threaded portion includes quad lead threads.

2. The spine stabilization system of claim 1, wherein the one or more flexible couplers are configured to attach to each other.

3. The spine stabilization system of claim 1, wherein the one or more flexible couplers are configured to attach to one of the rigid rods.

4. The spine stabilization system of claim 1, wherein the stem of the one or more flexible couplers is either curved or straight.

5. The spine stabilization system of claim 1, wherein the stem of the one or more flexible couplers has a threaded end.

6. The spine stabilization system of claim 5, wherein the flexible main body has as the recess a threaded opening for threaded attachment to a stem of another flexible coupler.

7. The spine stabilization system of claim 5, wherein the recess is threaded.

8. The spine stabilization system of claim 1, wherein the elongated shaft of the one or more rigid rods is either curved or straight.

9. The spine stabilization system of claim 1, wherein the elongated shaft of the one or more rigid rods has a threaded end.

10. The spine stabilization system of claim 9, wherein the flexible main body has as the recess a threaded opening for threaded attachment to the elongated shaft of one of the rigid rods.

11. The spine stabilization system of claim 9, wherein the flexible main body comprises at least one coil unit.

12. The spine stabilization system of claim 1, wherein the one or more flexible couplers are differently sized.

13. The spine stabilization system of claim 1, wherein the one or more rigid rods are differently sized.

14. An implantable, modular spine stabilization system, comprising:
    one or more flexible couplers configured to dynamically stabilize a spinal segment of a patient's spine, each flexible coupler having a flexible main body at a proximal end and a bendable stem extending therefrom, each of the one or more flexible couplers having a recess in the flexible main body and proximate to one or more exterior openings and/or slots on an exterior of the flexible main body, the recess configured to receive another of the one or more flexible couplers or a rigid rod, the recess attached within the flexible coupler at a proximal end region such that flexibility of the flexible coupler is maintained, wherein the flexible main body is flexible from a proximal end to a distal end thereof;
    one or more rigid rods configured to rigidly stabilize a spinal segment of the patient's spine, each rigid rod having an elongated shaft and configured to be secured in one of the one or more flexible couplers; and
    one or more bone fasteners configured to attach the one or more flexible couplers or rigid rods to the patient's spine, each of the one or more bone fasteners comprising a head portion including a cavity, and a shank portion extending from the head portion, the shank portion including an elongated shaft extending to a distal tip, the shank portion having an enlarged head captured within the cavity of the head portion and being defined by a first leading threaded portion adjacent the distal tip.

15. The spine stabilization system of claim 14, wherein the one or more flexible couplers are configured to attach to each other.

16. The spine stabilization system of claim 14, wherein the one or more flexible couplers are configured to attach to one of the rigid rods via threaded engagement.

17. The spine stabilization system of claim 14, wherein the stem of the one or more flexible couplers is either curved or straight.

18. The spine stabilization system of claim 14, wherein the stem of the one or more flexible couplers has a threaded end.

19. The spine stabilization system of claim 14, wherein the elongated shaft of the one or more rigid rods is either curved or straight.

20. The spine stabilization system of claim 14, wherein the elongated shaft of the one or more rigid rods has a threaded end.

* * * * *